(12) United States Patent
Czarnik

(10) Patent No.: US 7,745,480 B2
(45) Date of Patent: Jun. 29, 2010

(54) DEUTERIUM-ENRICHED ATORVASTATIN

(75) Inventor: Anthony W. Czarnik, Reno, NV (US)

(73) Assignee: Protia, LLC, Reno, NV (US)

( * ) Notice: Subject to any disclaimer, the term of this patent is extended or adjusted under 35 U.S.C. 154(b) by 0 days.

(21) Appl. No.: 12/098,198

(22) Filed: Apr. 4, 2008

(65) Prior Publication Data

US 2008/0280971 A1 Nov. 13, 2008

Related U.S. Application Data

(63) Continuation of application No. 11/745,704, filed on May 8, 2007, now abandoned.

(51) Int. Cl.
*A61K 31/40* (2006.01)
*C07D 207/00* (2006.01)

(52) U.S. Cl. .................................. 514/423; 548/537

(58) Field of Classification Search ............... 514/423; 548/537
See application file for complete search history.

(56) References Cited

U.S. PATENT DOCUMENTS 5,273,995 A * 12/1993 Roth ............................ 514/422

2004/0248972 A1 12/2004 Lockhart et al.

FOREIGN PATENT DOCUMENTS

WO 95/26325 A1 10/1995

OTHER PUBLICATIONS

Kushner, D.J.; Pharmacological Uses and Perspectives of Heavy Water and Deuterated Compounds; Canadian Journal of Physiology and Pharmacology 1999, 77(2), 79-88.
Woo et al., Atorvastatin, an HMG-CoA Reductase Inhibitor and Effective Lipid-Regulating Agent. Part III. "Synthesis of [2H5]-, [13C8], and [13C7, 15N] Artorvastatin and Their Application in Metabolic and Pharmacokinetic Studies." J. Labelled Cpd. Radiopharm. 42, 135-145 (1999).
Chen et al., "Synthesis of Deuterium-Labeled Atorvastatin and Its Metabolites for Use as Internal Standards in A LC/MS/MS Method Developed for Quantitation of the Drug and Its Metabolites in Human Serum." J. Labelled Cpd. Radiopharm. 43(3), 135-145 (2000).
Whitfield et al., "A Study Utilizing Stable Isotope Technique to Provide Information for the Design of Pivotal Atorvastatin Tablet Bioequivalence Studies." Pharm. Res. 14, No. 11, Suppl., S250 (1997). (Abstract only).
Valesky, R.J., Automated enzyme inhibition assay method for the determination of atorvastatin-derived HMG-CoA reductase inhibitors in human plasma using radioactivity detection, J. Pharmacol. & Toxicol. 2008, 57, 61-69.

* cited by examiner

*Primary Examiner*—Joseph R Kosack
(74) *Attorney, Agent, or Firm*—Vance Intellectual Property, PC

(57) ABSTRACT

The present application describes deuterium-enriched atorvastatin, pharmaceutically acceptable salt forms thereof, and methods of treating using the same.

99 Claims, No Drawings

DEUTERIUM-ENRICHED ATORVASTATIN

FIELD OF THE INVENTION

This invention relates generally to deuterium-enriched atorvastatin, pharmaceutical compositions containing the same, and methods of using the same.

BACKGROUND OF THE INVENTION

Atorvastatin, shown below, is a well known competitive inhibitor of HMG-CoA reductase.

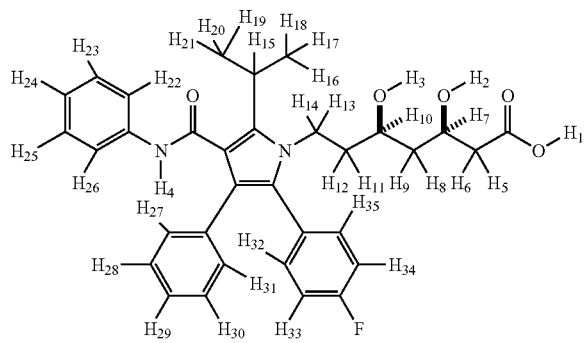

Since atorvastatin is a known and useful pharmaceutical, it is desirable to discover novel derivatives thereof. Atorvastatin is described in U.S. Pat. No. 5,273,995; the contents of which are incorporated herein by reference.

BRIEF SUMMARY OF THE INVENTION

Accordingly, one object of the present invention is to provide deuterium-enriched atorvastatin or a pharmaceutically acceptable salt thereof.

It is another object of the present invention to provide pharmaceutical compositions comprising a pharmaceutically acceptable carrier and a therapeutically effective amount of at least one of the deuterium-enriched compounds of the present invention or a pharmaceutically acceptable salt thereof.

It is another object of the present invention to provide a method for treating a disease selected from dyslipidaemia and/or combined hyperlipidemia, comprising administering to a host in need of such treatment a therapeutically effective amount of at least one of the deuterium-enriched compounds of the present invention or a pharmaceutically acceptable salt thereof.

It is another object of the present invention to provide a novel deuterium-enriched atorvastatin or a pharmaceutically acceptable salt thereof for use in therapy.

It is another object of the present invention to provide the use of a novel deuterium-enriched atorvastatin or a pharmaceutically acceptable salt thereof for the manufacture of a medicament (e.g., for the treatment of dyslipidaemia and/or combined hyperlipidemia).

These and other objects, which will become apparent during the following detailed description, have been achieved by the inventor's discovery of the presently claimed deuterium-enriched atorvastatin.

DETAILED DESCRIPTION OF PREFERRED EMBODIMENTS

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

The present invention provides deuterium-enriched atorvastatin or a pharmaceutically acceptable salt thereof. There are thirty-five hydrogen atoms in the atorvastatin portion of atorvastatin as show by variables $R_1$-$R_{35}$ in formula I below.

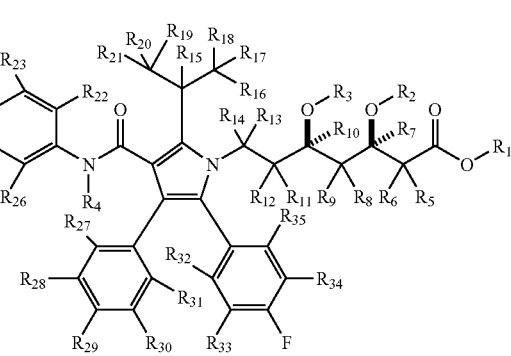

I

The hydrogens present on atorvastatin have different capacities for exchange with deuterium. The hydrogen (or deuterium) atoms represented by $R_1$-$R_4$ are easily exchangeable with water under physiological conditions. Thus, if any of $R_1$-$R_4$ are deuterium, they will readily exchange with a proton after administration to a patient. The hydrogens represented by $R_5$ and $R_6$ are exchangeable with deuterium in the presence of acid (e.g., $D_2SO_4/D_2O$) or base (e.g., NaOD/$D_2O$), but care must be taken in light of the potential formation of a lactone and the possible hydrolysis of the amide linkage. Treatment with strong acid (e.g., $D_2SO_4/D_2O$) may cause the exchange of certain of the aromatic protons (selected from $R_{22}$-$R_{35}$) for deuterium. The hydrogens represented by $R_7$-$R_{21}$, and certain of $R_{22}$-$R_{35}$, are non-exchangeable or essentially non-exchangeable. Deuterium enrichment can only reasonably occur by using deuterated reagents, starting materials, or intermediates during the synthesis of atorvastatin.

The present invention is based on increasing the amount of deuterium present in atorvastatin above its natural abundance. This increasing is called enrichment or deuterium-enrichment. If not specifically noted, the percentage of enrichment refers to the percentage of deuterium present in the compound, mixture of compounds, or composition. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Since there are 35 hydrogens in atorvastatin, replacement of a single hydrogen atom with deuterium would result in a molecule with about 3% deuterium enrichment. In order to achieve enrichment less than about 3%, but above the natural abundance, only partial deuteration of one site is required. Thus, less than about 3% enrichment would still refer to deuterium-enriched atorvastatin.

With the natural abundance of deuterium being 0.015%, one would expect that for approximately every 6,667 molecules of atorvastatin (1/0.00015=6,667), there is one naturally occurring molecule with one deuterium present. Since atorvastatin has 35 positions, one would roughly expect that for approximately every 233,345 molecules of atorvastatin (35×6,667), all 35 different, naturally occurring, mono-deuterated atorvastatins would be present. This approximation is a rough estimate as it doesn't take into account the different exchange rates of the hydrogen atoms on atorvastatin. For naturally occurring molecules with more than one deuterium, the numbers become vastly larger. In view of this natural abundance, the present invention, in an embodiment, relates to an amount of an deuterium enriched compound, whereby the enrichment recited will be more than naturally occurring deuterated molecules.

In view of the natural abundance of deuterium-enriched atorvastatin, the present invention also relates to isolated or purified deuterium-enriched atorvastatin. The isolated or purified deuterium-enriched atorvastatin is a group of molecules whose deuterium levels are above the naturally occurring levels (e.g., 3%). The isolated or purified deuterium-enriched atorvastatin can be obtained by techniques known to those of skill in the art (e.g., see the syntheses described below).

The present invention also relates to compositions comprising deuterium-enriched atorvastatin. The compositions require the presence of deuterium-enriched atorvastatin which is greater than its natural abundance. For example, the compositions of the present invention can comprise (a) a μg of a deuterium-enriched atorvastatin; (b) a mg of a deuterium-enriched atorvastatin; and, (c) a gram of a deuterium-enriched atorvastatin.

In an embodiment, the present invention provides an amount of a novel deuterium-enriched atorvastatin.

Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another embodiment, the present invention provides a novel, deuterium enriched compound of formula I or a pharmaceutically acceptable salt thereof.

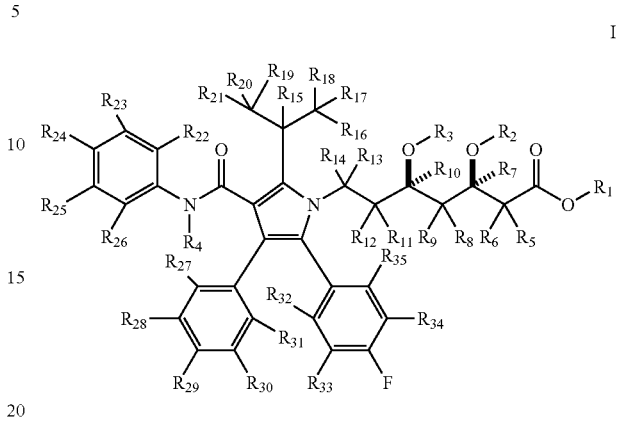

wherein $R_1$-$R_{35}$ are independently selected from H and D; and the abundance of deuterium in $R_1$-$R_{35}$ is at least 3%, provided that if $R_{22\text{-}26}$ are all D or $R_{27\text{-}31}$ are all D, then at least one other R is D. The abundance can also be (a) at least 9%, (b) at least 14%, (c) at least 20%, (d) at least 26%, (e) at least 31%, (f) at least 37%, (g) at least 43%, (h) at least 49%, (i) at least 54%, (j) at least 60%, (k) at least 66%, (l) at least 71%, (m) at least 77%, (n) at least 83%, (o) at least 89%, (p) at least 94%, and (q) 100%.

In another embodiment, if $R_{22\text{-}26}$ are all D or $R_{27\text{-}31}$ are all D, then at least one of $R_{5\text{-}21}$ is D.

In another embodiment, the present invention provides a novel, deuterium enriched compound of formula I or a pharmaceutically acceptable salt thereof, wherein the abundance of deuterium in $R_1$-$R_4$ is at least 25%. The abundance can also be (a) at least 50%, (b) at least 75%, and (c) 100%.

In another embodiment, the present invention provides a novel, deuterium enriched compound of formula I or a pharmaceutically acceptable salt thereof, wherein the abundance of deuterium in $R_5$-$R_6$ is at least 50%. The abundance can also be 100%.

In another embodiment, the present invention provides a novel, deuterium enriched compound of formula I or a pharmaceutically acceptable salt thereof, wherein the abundance of deuterium in $R_{22}$-$R_{35}$ is at least 7%. The abundance can also be (a) at least 14%, (b) at least 21%, (c) at least 29%, (d) at least 36%, (e) at least 43%, (f) at least 50%, (g) at least 57%, (h) at least 64%, (i) at least 71%, (j) at least 79%, (k) at least 86%, (l) at least 93%, and (m) 100%.

In another embodiment, the present invention provides a novel, deuterium enriched compound of formula I, wherein the abundance of deuterium in $R_7$-$R_{35}$ is at least 3%, provided that if $R_{27\text{-}31}$ are D, then at least one other R is D. The abundance can also be (a) at least 7%, (b) at least 14%, (c) at least 21%, (d) at least 28%, (e) at least 34%, (f) at least 41%, (g) at least 48%, (h) at least 55%, (i) at least 62%, (j) at least 69%, (k) at least 76%, (l) at least 83%, (m) at least 90%, (n) at least 97%, and (o) 100%.

In another embodiment, the present invention provides a novel, deuterium enriched compound of formula I or a pharmaceutically acceptable salt thereof, wherein the abundance of deuterium in $R_1$-$R_6$ is at least 17%. The abundance can also be (a) at least 33%, (b) at least 50%, (c) at least 67%, (d) at least 83%, and (e) 100%.

In another embodiment, the present invention provides a novel, deuterium enriched compound of formula I or a pharmaceutically acceptable salt thereof, wherein the abundance of deuterium in $R_1$-$R_4$ and $R_{22}$-$R_{35}$ is at least 6%, provided that if $R_{27-31}$ are D, then at least one other R is D. The abundance can also be (a) at least 11%, (b) at least 22%, (c) at least 33%, (d) at least 44%, (e) at least 56%, (f) at least 67%, (g) at least 78%, (h) at least 89%, and (i) 100%.

In another embodiment, the present invention provides a novel, deuterium enriched compound of formula I or a pharmaceutically acceptable salt thereof, wherein the abundance of deuterium in $R_1$-$R_4$ and $R_7$-$R_{35}$ is at least 3%, provided that if $R_{27-31}$ are D, then at least one other R is D. The abundance can also be (a) at least 6%, (b) at least 12%, (c) at least 18%, (d) at least 24%, (e) at least 30%, (f) at least 36%, (g) at least 42%, (h) at least 48%, (i) at least 55%, (j) at least 60%, (k) at least 67%, (l) at least 73%, (m) at least 79%, (n) at least 85%, (o) at least 91%, (p) at least 97%, and (q) 100%.

In another embodiment, the present invention provides a novel, deuterium enriched compound of formula I or a pharmaceutically acceptable salt thereof, wherein the abundance of deuterium in $R_5$-$R_6$ and $R_{22}$-$R_{35}$ is at least 6%, provided that if $R_{27-31}$ are D, then at least one other R is D. The abundance can also be (a) at least 13%, (b) at least 19%, (c) at least 25%, (d) at least 31%, (e) at least 38%, (f) at least 44%, (g) at least 50%, (h) at least 56%, (i) at least 63%, (j) at least 69%, (k) at least 75%, (l) at least 81%, (m) at least 88%, (n) at least 94%, and (o) 100%.

In another embodiment, the present invention provides a novel, deuterium enriched compound of formula I or a pharmaceutically acceptable salt thereof, wherein the abundance of deuterium in $R_5$-$R_{35}$ is at least 3%, provided that if $R_{27-31}$ are D, then at least one other R is D. The abundance can also be (a) at least 6%, (b) at least 13%, (c) at least 19%, (d) at least 26%, (e) at least 32%, (f) at least 39%, (g) at least 45%, (h) at least 52%, (i) at least 58%, (j) at least 65%, (k) at least 71%, (l) at least 77%, (m) at least 84%, (n) at least 90%, (o) at least 97%, and (p) 100%.

In another embodiment, the present invention provides a novel, deuterium enriched compound of formula I or a pharmaceutically acceptable salt thereof, wherein the abundance of deuterium in $R_1$-$R_6$ and $R_{22}$-$R_{35}$ is at least 5%, provided that if $R_{27-31}$ are D, then at least one other R is D. The abundance can also be (a) at least 10%, (b) at least 15%, (c) at least 20%, (d) at least 25%, (e) at least 30%, (f) at least 35%, (g) at least 45%, (h) at least 50%, (i) at least 55%, (j) at least 60%, (k) at least 65%, (l) at least 75%, (m) at least 80%, (n) at least 85%, (o) at least 90%, (p) at least 95%, and (q) 100%.

In another embodiment, the present invention provides a novel, deuterium enriched compound of formula I or a pharmaceutically acceptable salt thereof, wherein the abundance of deuterium in $R_{13}$-$R_{14}$ is at least 50%. The abundance can also be (a) at least 100%.

In another embodiment, the present invention provides a novel, deuterium enriched compound of formula I or a pharmaceutically acceptable salt thereof, wherein the abundance of deuterium in $R_5$-$R_6$ and $R_8$-$R_9$ is at least 25%. The abundance can also be (a) at least 50%, (b) at least 75%, and (c) 100%.

In another embodiment, the present invention provides a novel, deuterium enriched compound of formula I or a pharmaceutically acceptable salt thereof, wherein the abundance of deuterium in $R_{32}$-$R_{35}$ is at least 25%. The abundance can also be (a) at least 50%, (b) at least 75%, and (c) 100%.

In another embodiment, the present invention provides a novel, deuterium enriched compound of formula I or a pharmaceutically acceptable salt thereof, wherein the abundance of deuterium in $R_{22}$-$R_{26}$ is at least 20%. The abundance can also be (a) at least 40%, (b) at least 60%, (c) at least 80%, and (d) 100%.

In another embodiment, the present invention provides a novel, deuterium enriched compound of formula I or a pharmaceutically acceptable salt thereof, wherein the abundance of deuterium in $R_{15}$-$R_{21}$ is at least 7%. The abundance can also be (a) at least 14%, (b) at least 29%, (c) at least 43%, (d) at least 57%, (e) at least 71%, (f) at least 86%, and (g) 100%.

In another embodiment, the present invention provides a novel, deuterium enriched compound of formula I or a pharmaceutically acceptable salt thereof, wherein the abundance of deuterium in $R_5$-$R_{14}$ is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides an isolated novel, deuterium enriched compound of formula I or a pharmaceutically acceptable salt thereof.

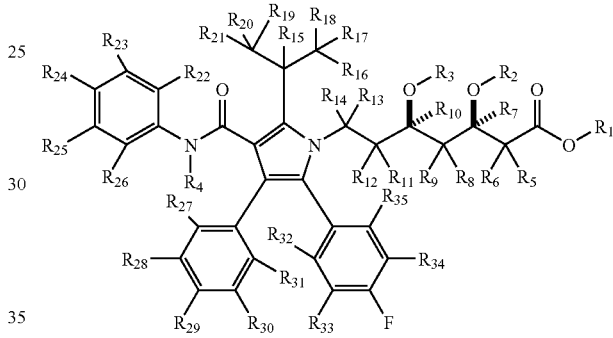

I wherein $R_1$-$R_{35}$ are independently selected from H and D; and the abundance of deuterium in $R_1$-$R_{35}$ is at least 3%, provided that if $R_{22-26}$ are all D or $R_{27-31}$ are all D, then at least one other R is D. The abundance can also be (a) at least 9%, (b) at least 14%, (c) at least 20%, (d) at least 26%, (e) at least 31%, (f) at least 37%, (g) at least 43%, (h) at least 49%, (i) at least 54%, (j) at least 60%, (k) at least 66%, (l) at least 71%, (m) at least 77%, (n) at least 83%, (o) at least 89%, (p) at least 94%, and (q) 100%.

In another embodiment, if $R_{22-26}$ are all D or $R_{27-31}$ are all D, then at least one of $R_{5-21}$ is D.

In another embodiment, the present invention provides an isolated novel, deuterium enriched compound of formula I or a pharmaceutically acceptable salt thereof, wherein the abundance of deuterium in $R_1$-$R_4$ is at least 25%. The abundance can also be (a) at least 50%, (b) at least 75%, and (c) 100%.

In another embodiment, the present invention provides an isolated novel, deuterium enriched compound of formula I or a pharmaceutically acceptable salt thereof, wherein the abundance of deuterium in $R_5$-$R_6$ is at least 50%. The abundance can also be 100%.

In another embodiment, the present invention provides an isolated novel, deuterium enriched compound of formula I or a pharmaceutically acceptable salt thereof, wherein the abundance of deuterium in $R_{22}$-$R_{35}$ is at least 7%, provided that if $R_{27-31}$ are D, then at least one other R is D. The abundance can also be (a) at least 14%, (b) at least 21%, (c) at least 29%, (d) at least 36%, (e) at least 43%, (f) at least 50%, (g) at least 57%, (h) at least 64%, (i) at least 71%, (j) at least 79%, (k) at least 86%, (l) at least 93%, and (m) 100%.

In another embodiment, the present invention provides an isolated novel, deuterium enriched compound of formula I, wherein the abundance of deuterium in $R_7$-$R_{35}$ is at least 3%, provided that if $R_{27\text{-}31}$ are D, then at least one other R is D. The abundance can also be (a) at least 7%, (b) at least 14%, (c) at least 21%, (d) at least 28%, (e) at least 34%, (f) at least 41%, (g) at least 48%, (h) at least 55%, (i) at least 62%, (j) at least 69%, (k) at least 76%, (l) at least 83%, (m) at least 90%, (n) at least 97%, and (o) 100%.

In another embodiment, the present invention provides an isolated novel, deuterium enriched compound of formula I or a pharmaceutically acceptable salt thereof, wherein the abundance of deuterium in $R_1$-$R_6$ is at least 17%. The abundance can also be (a) at least 33%, (b) at least 50%, (c) at least 67%, (d) at least 83%, and (e) 100%.

In another embodiment, the present invention provides a novel, deuterium enriched compound of formula I or a pharmaceutically acceptable salt thereof, wherein the abundance of deuterium in $R_1$-$R_4$ and $R_{22}$-$R_{35}$ is at least 6%, provided that if $R_{27\text{-}31}$ are D, then at least one other R is D. The abundance can also be (a) at least 11%, (b) at least 22%, (c) at least 33%, (d) at least 44%, (e) at least 56%, (f) at least 67%, (g) at least 78%, (h) at least 89%, and (i) 100%.

In another embodiment, the present invention provides an isolated novel, deuterium enriched compound of formula I or a pharmaceutically acceptable salt thereof, wherein the abundance of deuterium in $R_1$-$R_4$ and $R_7$-$R_{35}$ is at least 3%, provided that if $R_{27\text{-}31}$ are D, then at least one other R is D. The abundance can also be (a) at least 6%, (b) at least 12%, (c) at least 18%, (d) at least 24%, (e) at least 30%, (f) at least 36%, (g) at least 42%, (h) at least 48%, (i) at least 55%, (j) at least 60%, (k) at least 67%, (l) at least 73%, (m) at least 79%, (n) at least 85%, (o) at least 91%, (p) at least 97%, and (q) 100%.

In another embodiment, the present invention provides an isolated novel, deuterium enriched compound of formula I or a pharmaceutically acceptable salt thereof, wherein the abundance of deuterium in $R_5$-$R_6$ and $R_{22}$-$R_{35}$ is at least 6%, provided that if $R_{27\text{-}31}$ are D, then at least one other R is D. The abundance can also be (a) at least 13%, (b) at least 19%, (c) at least 25%, (d) at least 31%, (e) at least 38%, (f) at least 44%, (g) at least 50%, (h) at least 56%, (i) at least 63%, (j) at least 69%, (k) at least 75%, (l) at least 81%, (m) at least 88%, (n) at least 94%, and (o) 100%.

In another embodiment, the present invention provides an isolated novel, deuterium enriched compound of formula I or a pharmaceutically acceptable salt thereof, wherein the abundance of deuterium in $R_5$-$R_{35}$ is at least 3%, provided that if $R_{27\text{-}31}$ are D, then at least one other R is D. The abundance can also be (a) at least 6%, (b) at least 13%, (c) at least 19%, (d) at least 26%, (e) at least 32%, (f) at least 39%, (g) at least 45%, (h) at least 52%, (i) at least 58%, (j) at least 65%, (k) at least 71%, (l) at least 77%, (m) at least 84%, (n) at least 90%, (o) at least 97%, and (p) 100%.

In another embodiment, the present invention provides an isolated novel, deuterium enriched compound of formula I or a pharmaceutically acceptable salt thereof, wherein the abundance of deuterium in $R_1$-$R_6$ and $R_{22}$-$R_{35}$ is at least 5%, provided that if $R_{27\text{-}31}$ are D, then at least one other R is D. The abundance can also be (a) at least 10%, (b) at least 15%, (c) at least 20%, (d) at least 25%, (e) at least 30%, (f) at least 35%, (g) at least 45%, (h) at least 50%, (i) at least 55%, (j) at least 60%, (k) at least 65%, (l) at least 75%, (m) at least 80%, (n) at least 85%, (o) at least 90%, (p) at least 95%, and (q) 100%.

In another embodiment, the present invention provides an isolated novel deuterium enriched compound of formula I or a pharmaceutically acceptable salt thereof, wherein the abundance of deuterium in $R_5$-$R_6$ is at least 50%. The abundance can also be (a) at least 100.

In another embodiment, the present invention provides an isolated novel deuterium enriched compound of formula I or a pharmaceutically acceptable salt thereof, wherein the abundance of deuterium in $R_{13}$-$R_{14}$ is at least 50%. The abundance can also be (a) at least 100%.

In another embodiment, the present invention provides an isolated novel deuterium enriched compound of formula I or a pharmaceutically acceptable salt thereof, wherein the abundance of deuterium in $R_5$-$R_6$ and $R_8$-$R_9$ is at least 25%. The abundance can also be (a) at least 50%, (b) at least 75%, and (c) 100%.

In another embodiment, the present invention provides an isolated novel deuterium enriched compound of formula I or a pharmaceutically acceptable salt thereof, wherein the abundance of deuterium in $R_{32}$-$R_{35}$ is at least 25%. The abundance can also be (a) at least 50%, (b) at least 75%, and (c) 100%.

In another embodiment, the present invention provides an isolated novel deuterium enriched compound of formula I or a pharmaceutically acceptable salt thereof, wherein the abundance of deuterium in $R_{22}$-$R_{26}$ is at least 20%. The abundance can also be (a) at least 40%, (b) at least 60%, (c) at least 80%, and (d) 100%.

In another embodiment, the present invention provides an isolated novel deuterium enriched compound of formula I or a pharmaceutically acceptable salt thereof, wherein the abundance of deuterium in $R_{15}$-$R_{21}$ is at least 7%. The abundance can also be (a) at least 14%, (b) at least 29%, (c) at least 43%, (d) at least 57%, (e) at least 71%, (f) at least 86%, and (g) 100%.

In another embodiment, the present invention provides an isolated novel deuterium enriched compound of formula I or a pharmaceutically acceptable salt thereof, wherein the abundance of deuterium in $R_5$-$R_{14}$ is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides novel mixture of deuterium enriched compounds of formula I or a pharmaceutically acceptable salt thereof.

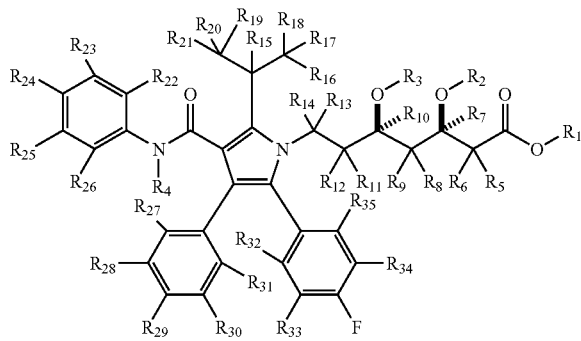

I wherein $R_1$-$R_{35}$ are independently selected from H and D; and the abundance of deuterium in $R_1$-$R_{35}$ is at least 3%, provided that if $R_{22\text{-}26}$ are all D or $R_{27\text{-}31}$ are all D, then at least one other R is D. The abundance can also be (a) at least 9%, (b) at least 14%, (c) at least 20%, (d) at least 26%, (e) at least 31%, (f) at least 37%, (g) at least 43%, (h) at least 49%, (i) at least 54%, (j) at least 60%, (k) at least 66%, (l) at least 71%, (m) at least 77%, (n) at least 83%, (o) at least 89%, (p) at least 94%, and (q) 100%.

In another embodiment, if $R_{22-26}$ are all D or $R_{27-31}$ are all D, then at least one of $R_{5-21}$ is D.

In another embodiment, the present invention provides a novel mixture of deuterium enriched compounds of formula I or a pharmaceutically acceptable salt thereof, wherein the abundance of deuterium in $R_1$-$R_4$ is at least 25%. The abundance can also be (a) at least 50%, (b) at least 75%, and (c) 100%.

In another embodiment, the present invention provides a novel mixture of deuterium enriched compounds of formula I or a pharmaceutically acceptable salt thereof, wherein the abundance of deuterium in $R_5$-$R_6$ is at least 50%. The abundance can also be 100%.

In another embodiment, the present invention provides a novel mixture of deuterium enriched compounds of formula I or a pharmaceutically acceptable salt thereof, wherein the abundance of deuterium in $R_{22}$-$R_{35}$ is at least 7%, provided that if $R_{27-31}$ are D, then at least one other R is D. The abundance can also be (a) at least 14%, (b) at least 21%, (c) at least 29%, (d) at least 36%, (e) at least 43%, (f) at least 50%, (g) at least 57%, (h) at least 64%, (i) at least 71%, (j) at least 79%, (k) at least 86%, (l) at least 93%, and (m) 100%.

In another embodiment, the present invention provides a novel mixture of deuterium enriched compounds of formula I, wherein the abundance of deuterium in $R_7$-$R_{35}$ is at least 3%, provided that if $R_{27-31}$ are D, then at least one other R is D. The abundance can also be (a) at least 7%, (b) at least 14%, (c) at least 21%, (d) at least 28%, (e) at least 34%, (f) at least 41%, (g) at least 48%, (h) at least 55%, (i) at least 62%, (j) at least 69%, (k) at least 76%, (l) at least 83%, (m) at least 90%, (n) at least 97%, and (o) 100%.

In another embodiment, the present invention provides a novel mixture of deuterium enriched compound of formula I or a pharmaceutically acceptable salt thereof, wherein the abundance of deuterium in $R_1$-$R_6$ is at least 17%, provided that if $R_{27-31}$ are D, then at least one other R is D. The abundance can also be (a) at least 33%, (b) at least 50%, (c) at least 67%, (d) at least 83%, and (e) 100%.

In another embodiment, the present invention provides a novel, deuterium enriched compound of formula I or a pharmaceutically acceptable salt thereof, wherein the abundance of deuterium in $R_1$-$R_4$ and $R_{22}$-$R_{35}$ is at least 6%, provided that if $R_{27-31}$ are D, then at least one other R is D. The abundance can also be (a) at least 11%, (b) at least 22%, (c) at least 33%, (d) at least 44%, (e) at least 56%, (f) at least 67%, (g) at least 78%, (h) at least 89%, and (i) 100%.

In another embodiment, the present invention provides a novel mixture of deuterium enriched compounds of formula I or a pharmaceutically acceptable salt thereof, wherein the abundance of deuterium in $R_1$-$R_4$, $R_7$-$R_{21}$, and $R_{22}$-$R_{35}$ is at least 3%, provided that if $R_{27-31}$ are D, then at least one other R is D. The abundance can also be (a) at least 6%, (b) at least 12%, (c) at least 18%, (d) at least 24%, (e) at least 30%, (f) at least 36%, (g) at least 42%, (h) at least 48%, (i) at least 55%, (j) at least 60%, (k) at least 67%, (l) at least 73%, (m) at least 79%, (n) at least 85%, (o) at least 91%, (p) at least 97%, and (q) 100%.

In another embodiment, the present invention provides a novel mixture of deuterium enriched compounds of formula I or a pharmaceutically acceptable salt thereof, wherein the abundance of deuterium in $R_5$-$R_6$ and $R_{22}$-$R_{35}$ is at least 6%, provided that if $R_{27-31}$ are D, then at least one other R is D. The abundance can also be (a) at least 13%, (b) at least 19%, (c) at least 25%, (d) at least 31%, (e) at least 38%, (f) at least 44%, (g) at least 50%, (h) at least 56%, (i) at least 63%, (j) at least 69%, (k) at least 75%, (l) at least 81%, (m) at least 88%, (n) at least 94%, and (o) 100%.

In another embodiment, the present invention provides a novel mixture of deuterium enriched compounds of formula I or a pharmaceutically acceptable salt thereof, wherein the abundance of deuterium in $R_5$-$R_{35}$ is at least 3%, provided that if $R_{27-31}$ are D, then at least one other R is D. The abundance can also be (a) at least 6%, (b) at least 13%, (c) at least 19%, (d) at least 26%, (e) at least 32%, (f) at least 39%, (g) at least 45%, (h) at least 52%, (i) at least 58%, (j) at least 65%, (k) at least 71%, (l) at least 77%, (m) at least 84%, (n) at least 90%, (o) at least 97%, and (p) 100%.

In another embodiment, the present invention provides a novel mixture of deuterium enriched compounds of formula I or a pharmaceutically acceptable salt thereof, wherein the abundance of deuterium in $R_1$-$R_6$ and $R_{22}$-$R_{35}$ is at least 5%, provided that if $R_{27-31}$ are D, then at least one other R is D. The abundance can also be (a) at least 10%, (b) at least 15%, (c) at least 20%, (d) at least 25%, (e) at least 30%, (f) at least 35%, (g) at least 45%, (h) at least 50%, (i) at least 55%, (j) at least 60%, (k) at least 65%, (l) at least 75%, (m) at least 80%, (n) at least 85%, (o) at least 90%, (p) at least 95%, and (q) 100%.

In another embodiment, the present invention provides a mixture of deuterium enriched compound of formula I or a pharmaceutically acceptable salt thereof, wherein the abundance of deuterium in $R_5$-$R_6$ is at least 50%. The abundance can also be (a) at least 100.

In another embodiment, the present invention provides a mixture of deuterium enriched compound of formula I or a pharmaceutically acceptable salt thereof, wherein the abundance of deuterium in $R_{13}$-$R_{14}$ is at least 50%. The abundance can also be (a) at least 100%.

In another embodiment, the present invention provides a mixture of deuterium enriched compound of formula I or a pharmaceutically acceptable salt thereof, wherein the abundance of deuterium in $R_5$-$R_6$ and $R_8$-$R_9$ is at least 25%. The abundance can also be (a) at least 50%, (b) at least 75%, and (c) 100%.

In another embodiment, the present invention provides a mixture of deuterium enriched compound of formula I or a pharmaceutically acceptable salt thereof, wherein the abundance of deuterium in $R_{32}$-$R_{35}$ is at least 25%. The abundance can also be (a) at least 50%, (b) at least 75%, and (c) 100%.

In another embodiment, the present invention provides a mixture of deuterium enriched compound of formula I or a pharmaceutically acceptable salt thereof, wherein the abundance of deuterium in $R_{22}$-$R_{26}$ is at least 20%. The abundance can also be (a) at least 40%, (b) at least 60%, (c) at least 80%, and (d) 100%.

In another embodiment, the present invention provides a mixture of deuterium enriched compound of formula I or a pharmaceutically acceptable salt thereof, wherein the abundance of deuterium in $R_{15}$-$R_{21}$ is at least 7%. The abundance can also be (a) at least 14%, (b) at least 29%, (c) at least 43%, (d) at least 57%, (e) at least 71%, (f) at least 86%, and (g) 100%.

In another embodiment, the present invention provides a mixture of deuterium enriched compound of formula I or a pharmaceutically acceptable salt thereof, wherein the abundance of deuterium in $R_5$-$R_{14}$ is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides novel pharmaceutical compositions, comprising: a pharmaceutically acceptable carrier and a therapeutically effective amount of a deuterium-enriched compound of the present invention.

In another embodiment, the present invention provides a novel method for treating dyslipidaemia and/or combined hyperlipidemia comprising: administering to a patient in need thereof a therapeutically effective amount of a deuterium-enriched compound of the present invention.

In another embodiment, the present invention provides an amount of a deuterium-enriched compound of the present invention as described above for use in therapy.

In another embodiment, the present invention provides the use of an amount of a deuterium-enriched compound of the present invention for the manufacture of a medicament (e.g., for the treatment of dyslipidaemia and/or combined hyperlipidemia).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds of the present invention may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present invention.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, $Adv.\ Enzyme\ Regul.$ 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

Synthesis

Scheme 1 shows an example of how to prepare atorvastatin (see for example U.S. Pat. No. 5,273,995, $Tetrahedron\ Lett.$ 1992, 33, 2279, $Tetrahedron\ Lett.$ 1992, 33, 2283).

Scheme 1

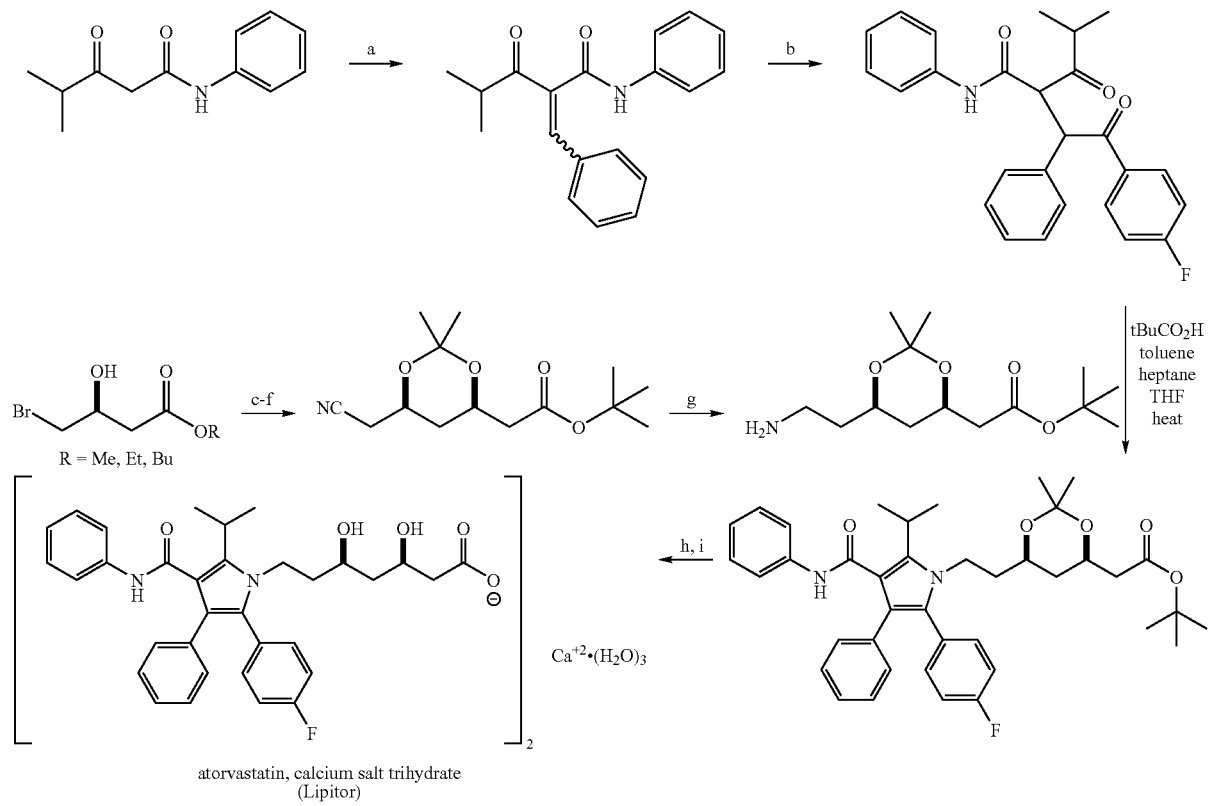

Scheme 2.

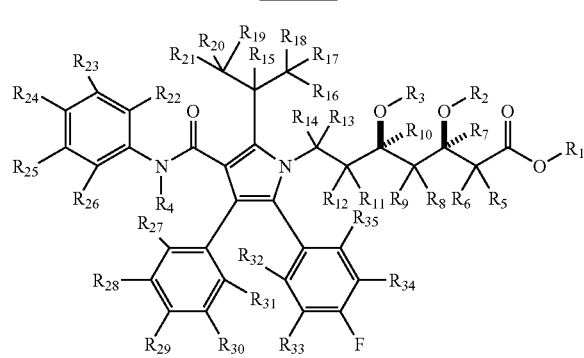

Atorvastatin itself may be used as a starting material for the synthesis of deuterated versions (other than deuteration of the physiologically exchangeable hydrogens or by exchange of protium for deuterium using catalytic acids and bases, vide supra). Atorvastatin is known (U.S. Pat. No. 5,273,995) to convert to a lactone under dehydrating conditions (Scheme 3). It may then be converted to the calcium salt (trihydrate) of atorvastatin using aqueous NaOH followed by treatment with a suitable calcium salt. If NaOD/$D_2$O/MeOD were used instead, the hydrogens $R_5$ and $R_6$ (see Scheme 2 for reference) should be exchanged during the lactone opening reaction to provide dideuterioatorvastatin calcium salt trihydrate, where $R_5$=$R_6$=D. In general, aromatic protons may be exchanged for deuterium under acidic conditions (e.g., $D_2SO_4$). The success of this exchange depends on the pi-basicity of the aromatic ring(s) at various positions. For atorvastatin, of the four aromatic rings, three bear hydrogens (see $R_{22}$-$R_{35}$ in Scheme 2). It should be possible to cause an acid-catalyzed exchange of some of these protons for deuterium without causing significant amounts of decomposition. Since atorvastatin contains a potentially acid sensitive amide group, exchange with deuterium under acidic conditions may occur with varying amounts of hydrolysis of the amide group. Further, lactonization will also probably occur. The lactone may be opened to atorvastatin (vide supra). As shown in Scheme 3, $D_2SO_4$ treatment should provide exchange of certain aromatic protons with deuterium. Recalling Scheme 2, $R_{22}$, $R_{24}$, and $R_{26}$ may be exchanged due to the activating effect of the amide nitrogen. The rate of exchange should be $R_{22}$=$R_{26}$>$R_{24}$. $R_{23}$ and $R_{25}$ will probably require conditions that are too harsh. The protons $R_{27}$, $R_{29}$, $R_{31}$, $R_{32}$, and $R_{35}$ may be exchangeable for deuterium under acidic conditions because of the activating effect of the pi-donating pyrrole ring, even though there is a deactivating fluorine atom on one of the rings. $R_{28}$, $R_{30}$, $R_{33}$, and $R_{34}$ will probably require conditions that are too harsh. Opening of the lactone will provide atorvastatin calcium salt trihydrate with deuterium at various aromatic positions as well as optionally at $R_5$ and $R_6$ if NaOD/$D_2$O/MeOD is used. If NaOH/$H_2$O/MeOH is used, $R_5$ and $R_6$ will remain protons.

Scheme 3.

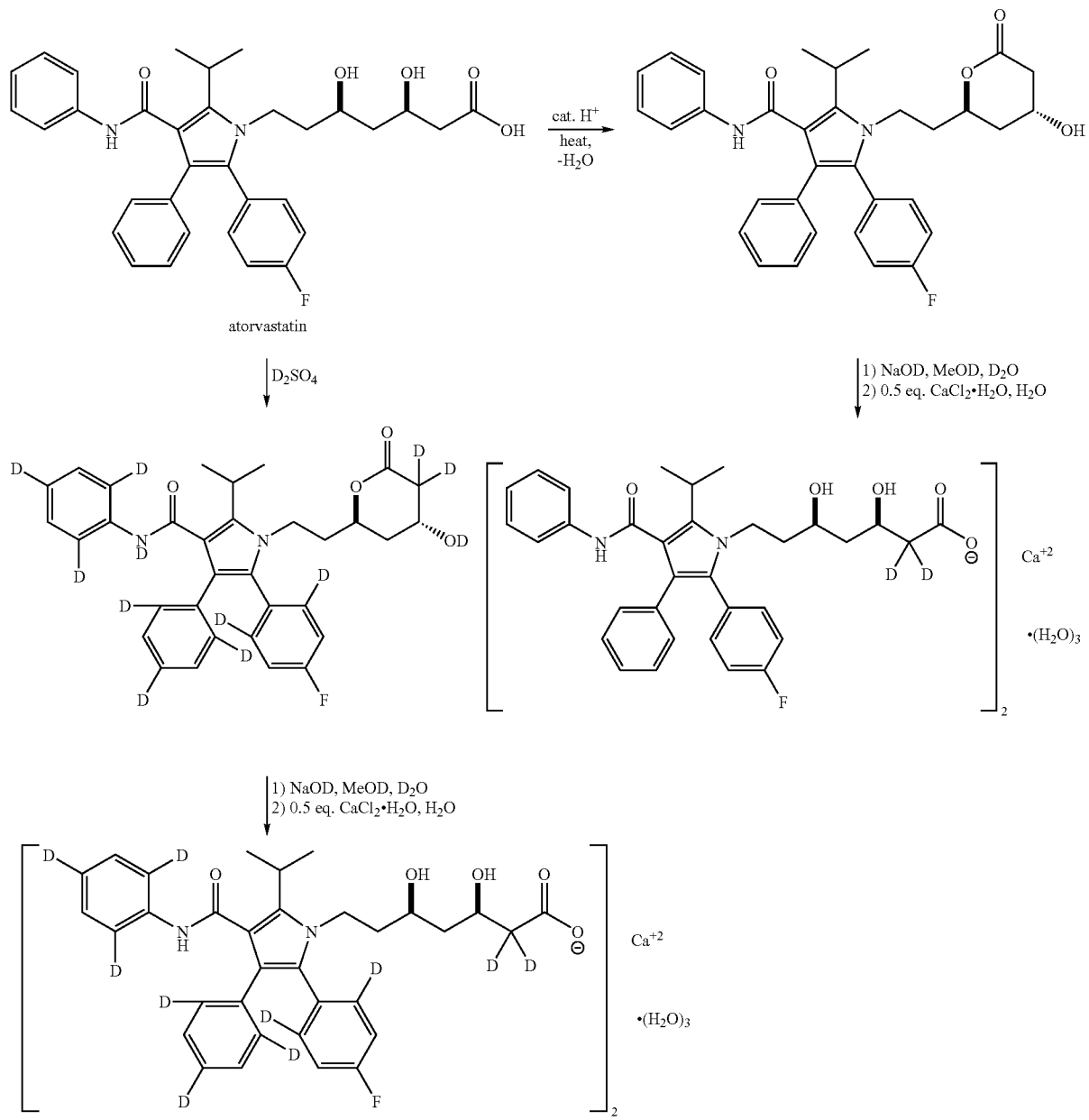

The synthesis of atorvastatin calcium trihydrate shown in Scheme 1 above offers several opportunities for incorporating deuterium during its preparation by the use of deuterated staffing materials or intermediates. A person skilled in the art of organic synthesis would recognize that various combinations of the deuterated species shown would allow the synthesis of many different deuterated atorvastatin analogs. Scheme 4 focuses on the preparation of various deuterated versions of the key 1,4-diketone 1 used in Scheme 1. In equation (1), condensation of Meldrum's acid with isobutyic acid chloride provides the known 1,3-dioxan-4,6-dione, which may then be condensed with commercially available pentadeuterioaniline to give the 1,3-dicarbonyl compound 2, which ultimately should produce atorvastatin with $R_{22}$-$R_{26}$=D (refer back to Scheme 2). Alternatively, the known heptadeuterioisobutyric acid chloride 3 could be used in a condensation with Meldrum's acid to give ultimately atorvastatin with $R_{15}$-$R_{21}$=D. Compounds 2 and 3 and atorvastatin analogs thereof are known (Chen, et al., *J. Labelled Cpd. Radiopharm.* 2000, 43, 261-270). These compounds were used to make atorvastatin lactone bearing deuteria, which could, in principle, be used to make atorvastatin with $R_{22}$-$R_{26}$=D. The actual transformation of the lactone to deuterated atorvastatin was not reported in this paper. In equation (2), treating the 1,3-dicarbonyl compound shown with MeOD/$D_2O$ should cause exchange of certain protons for deuterium, providing 4 after workup with $H_2O$, ultimately providing atorvastatin with $R_{15}$=D. The use of known 2,3,4,5,6-pentadeuteriobenzaldehyde in the condensation shown in equation (3) should provide 5, ultimately allowing the synthesis of atorvastatin with $R_{27}$-$R_{31}$=D. The use of the known 2,3,5,6-tetradeuterio-4-fluorobenzaldehyde in the condensation shown in equation (4) should provide 6, which should be useful for making atorvastatin with $R_{32}$-$R_{35}$=D. Again, a person skilled in the art of organic synthesis would recognize that these various deuterated starting materials and intermediates could be combined as necessary to produce a variety of deuterated versions of 1 and thus atorvastatin.

Deuterated starting materials and intermediates for the synthesis of various deuterated versions of the 1,4-diketone 1:

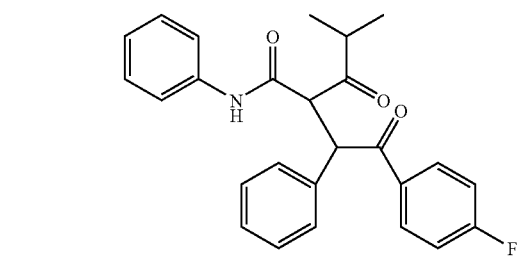

1
Scheme 4.

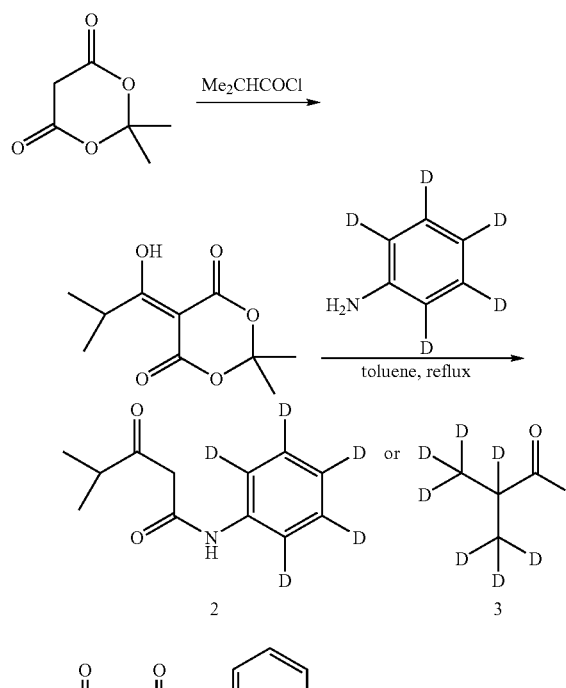

(1)

(2)

-continued

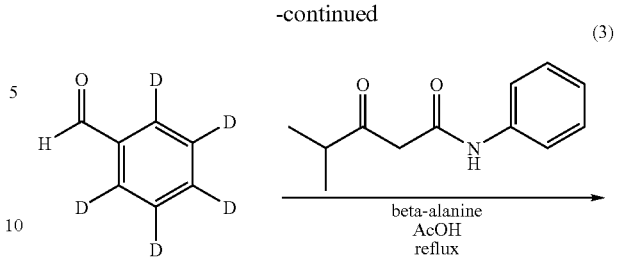

(3)

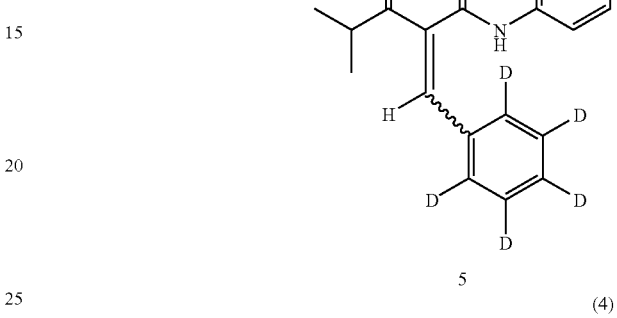

(4)

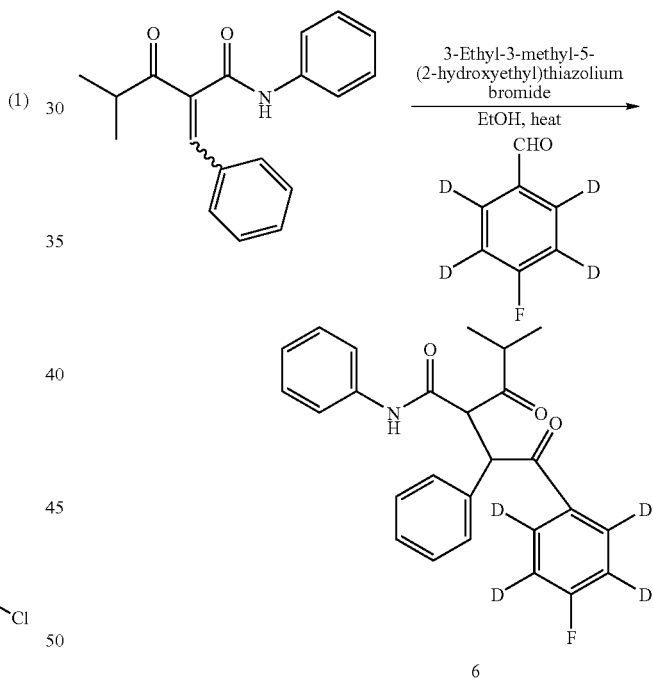

Scheme 5 shows the synthesis of various deuterated analogs of the amine 7 (refer back to Scheme 1). As shown in equation (5), the tetradeuterated bromide 8 may be prepared by enzymatic reduction (well-known on the protio compound) of the tetradeuterated bromoacetoacetate shown, which is prepared by simply exposing the starting material with deuterated methanol. A mild acid or base catalyst may be added to assist the exchange. Compound 8 should be useful for making atorvastatin with $R_8$, $R_9$, $R_{11}$, and $R_{12}$=D. Exposing the bromo alcohol the reagents from Scheme 1, except deuterated where appropriate, should provide 9, as shown in equation (6), ultimately providing atorvastatin with $R_5$-$R_7$=D. Compound 10 may be prepared by reduction of the nitrile with deuterium gas, as shown in equation (7). This should allow the synthesis of atorvastatin where $R_{13}$ and $R_{14}$ are deuterium. Again, a person skilled in the art of organic synthesis would recognize that these various deuterated starting materials and intermediates could be combined as necessary to produce a variety of deuterated versions of 7 and thus atorvastatin. Further, combination of various deuterated forms of 7 with various deuterated forms of 1 (see Scheme 4 and the discussion thereof) should provide further deuterated forms of atorvastatin and thus atorvastatin calcium trihydrate.

Deuterated starting materials and intermediates for the synthesis of various deuterated versions of the amine 7:

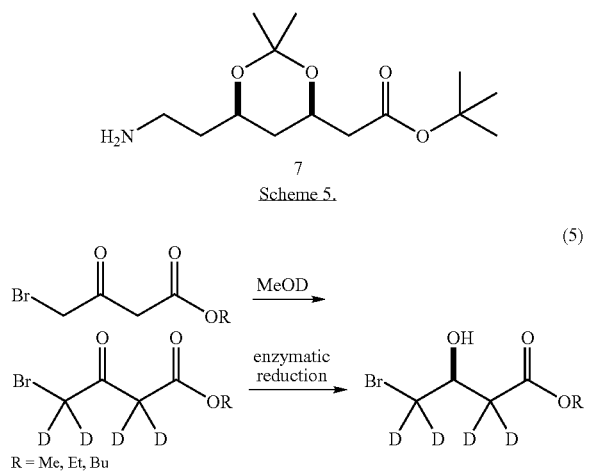

Scheme 5.

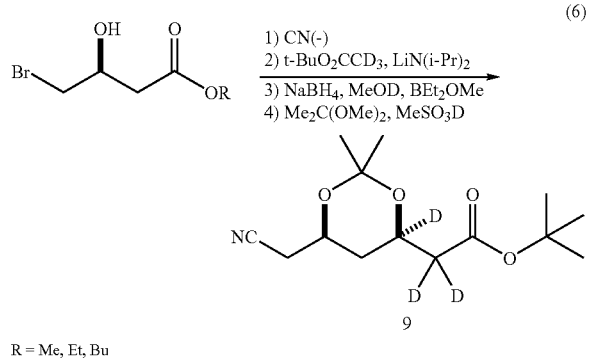

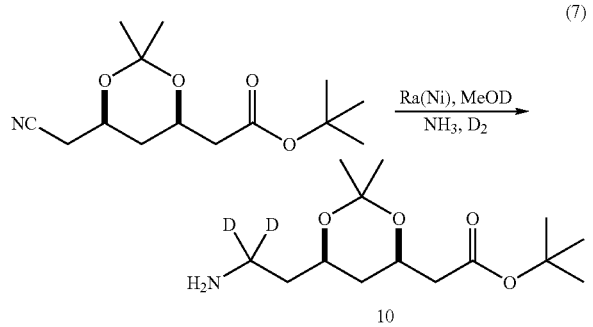

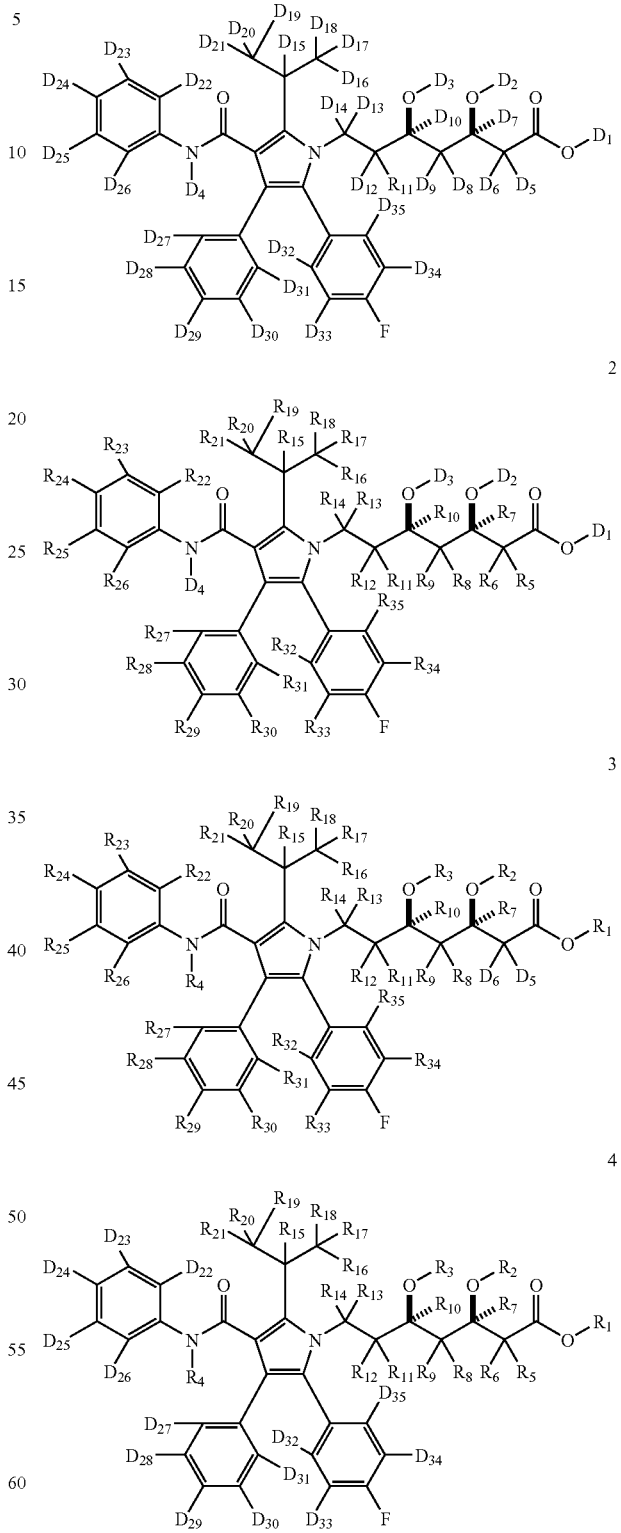

EXAMPLES

Table 1 provides compounds that are representative examples of the present invention. When one of $R_1$-$R_{35}$ is present, it is selected from H or D.

-continued
5
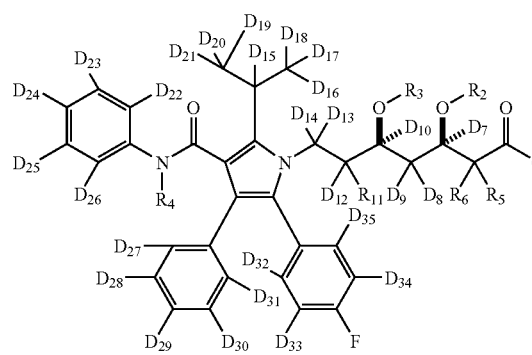
6
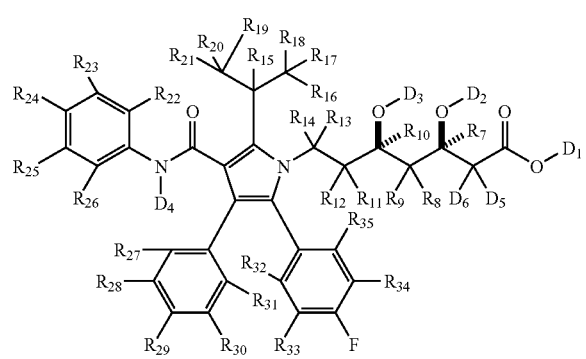
7
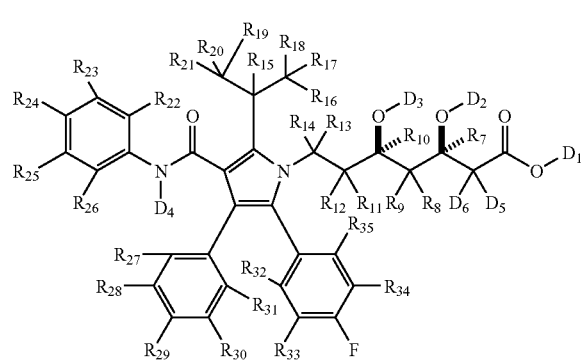
8
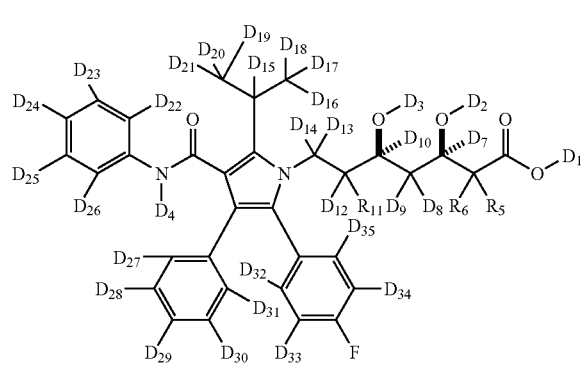
9
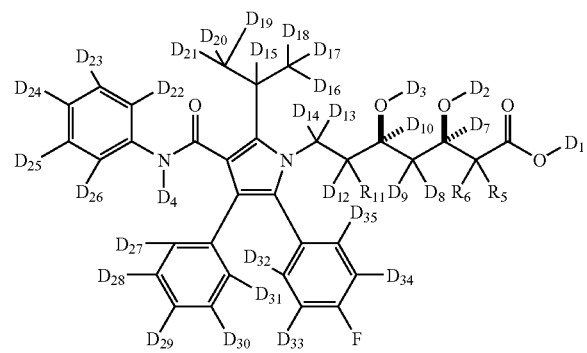
10
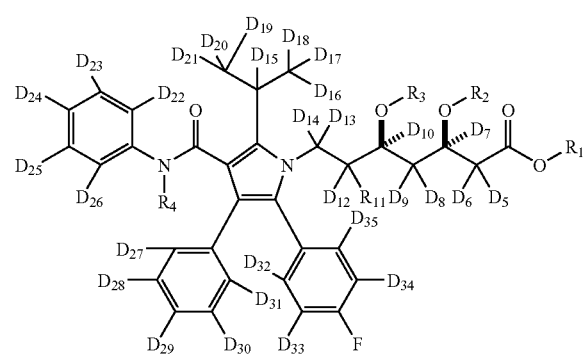
11
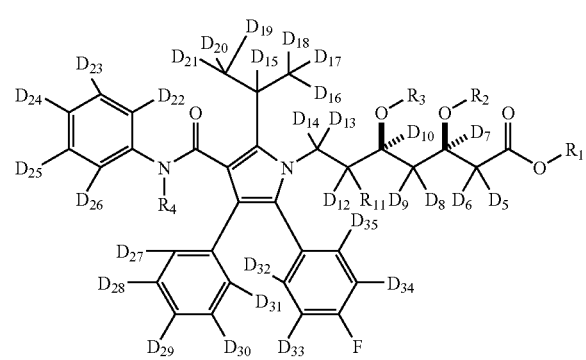
12
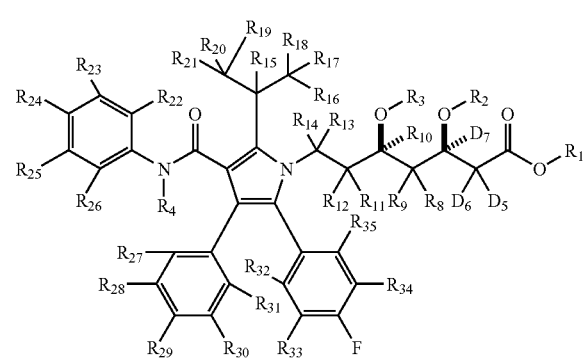

-continued
13
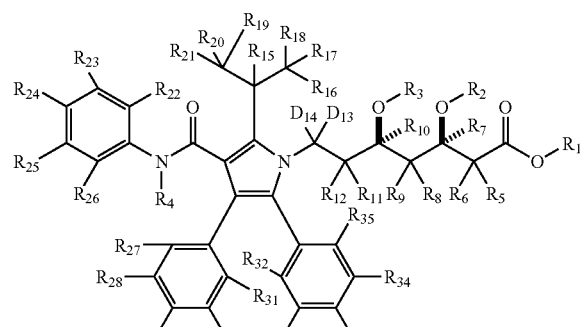
14
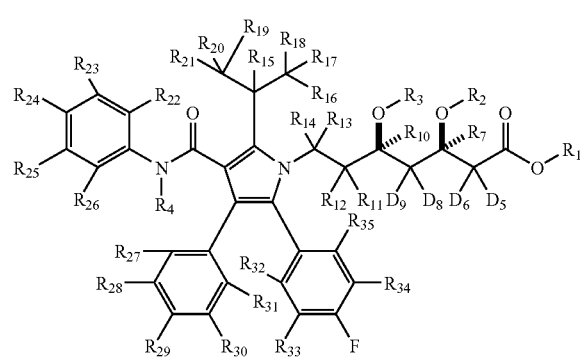
15
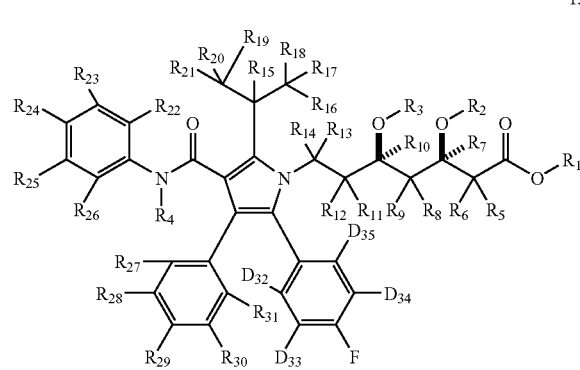
16
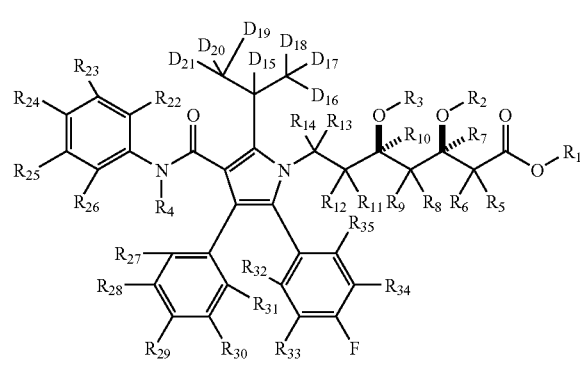
-continued
17
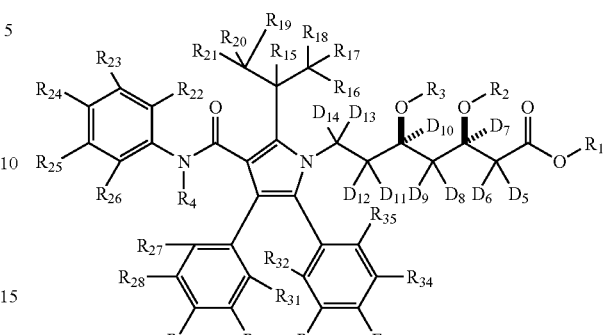
Table 2 provides compounds that are representative examples of the present invention. Where H is shown, it represents naturally abundant hydrogen.
18
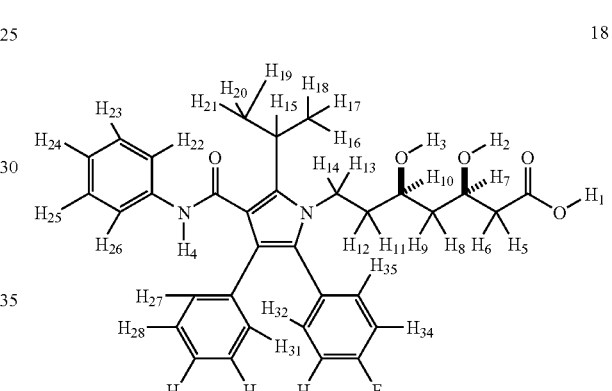
19
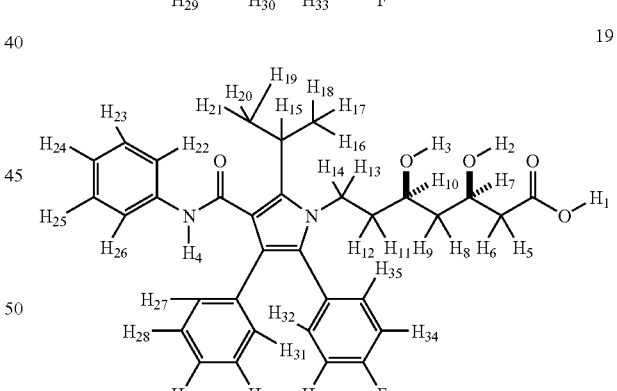

20
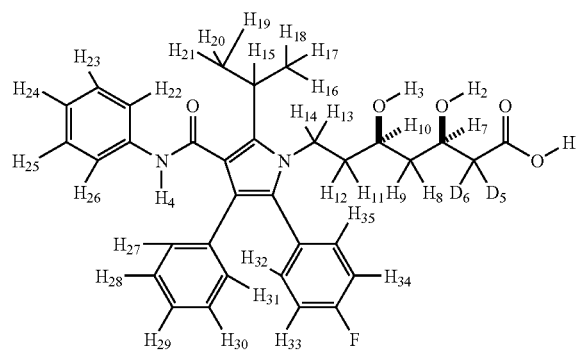
21
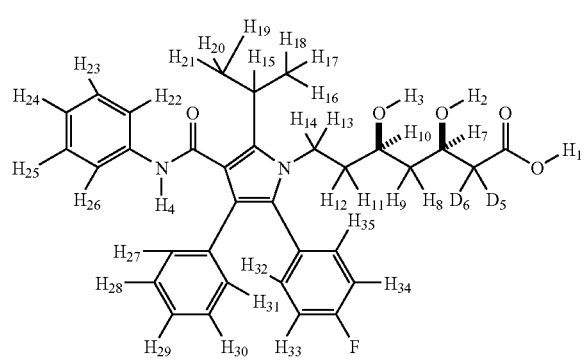
22
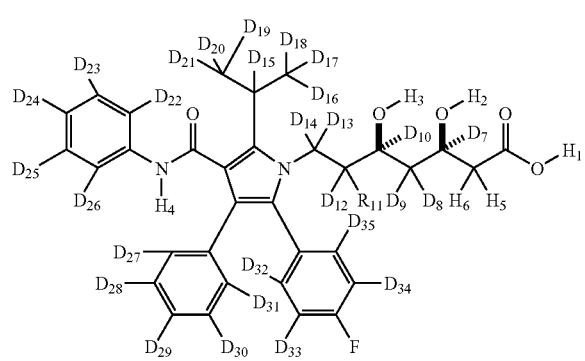
23
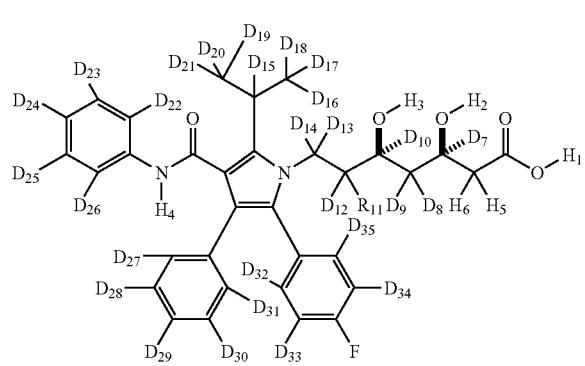
24
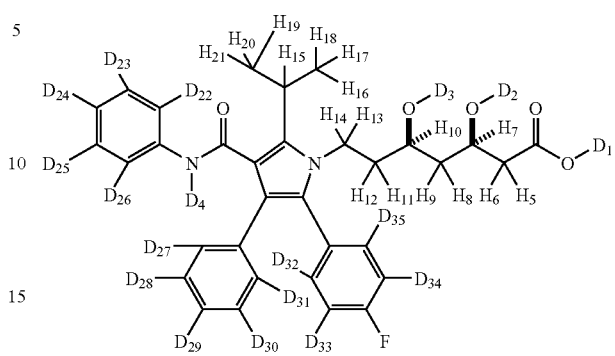
25
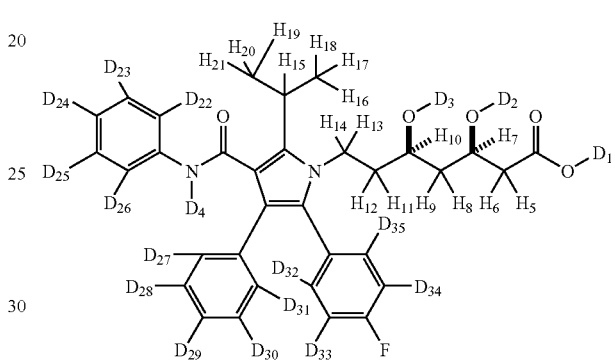
26
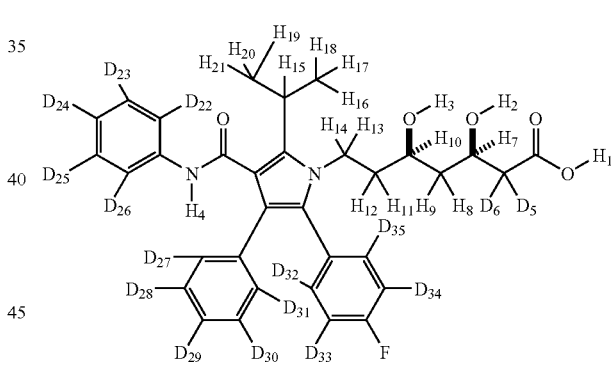
27
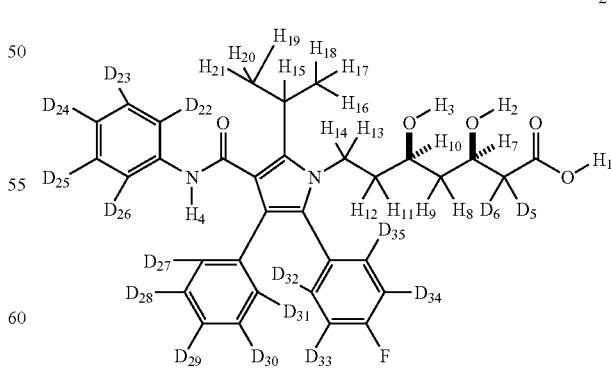

-continued

28
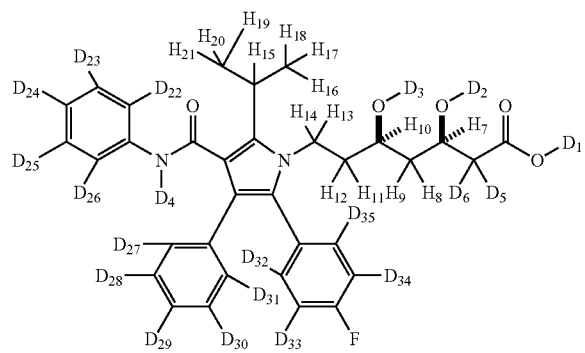

29
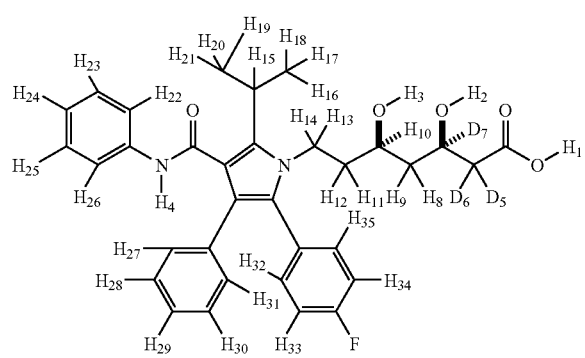

30
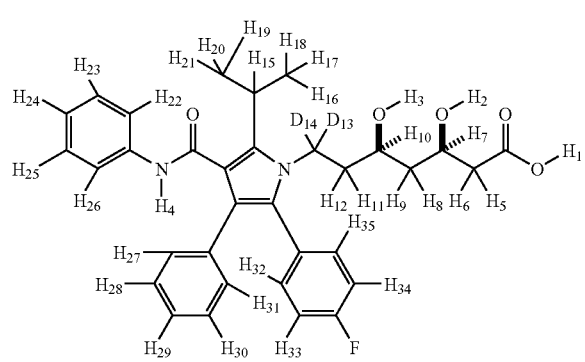

31
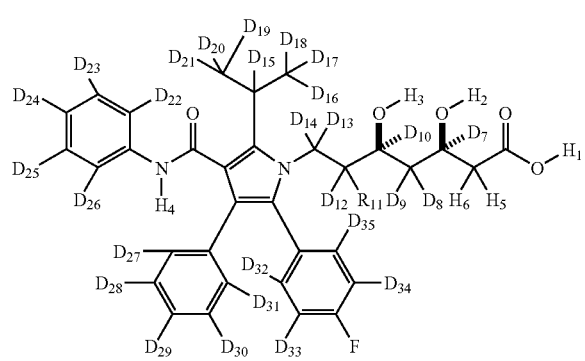

-continued

32
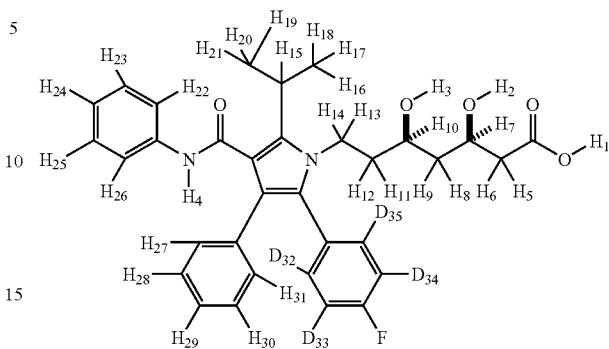

33
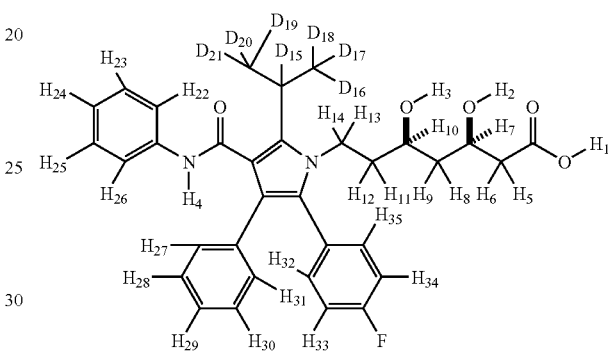

34
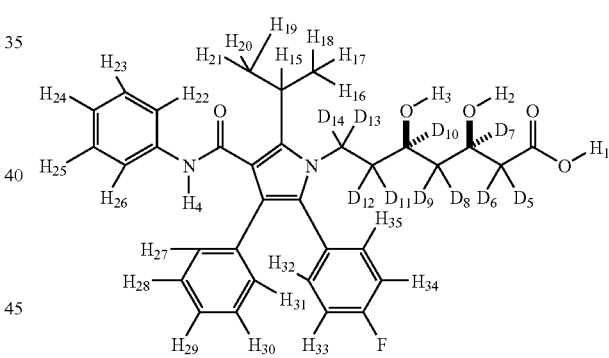

Numerous modifications and variations of the present invention are possible in light of the above teachings. It is therefore to be understood that within the scope of the appended claims, the invention may be practiced otherwise that as specifically described herein.

What is claimed is:

1. A deuterium-enriched compound of formula I or a pharmaceutically acceptable salt thereof:

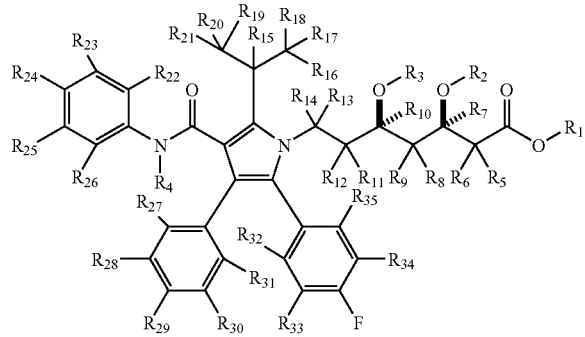

wherein $R_1$-$R_{35}$ are independently selected from H and D; and the abundance of deuterium in $R_{32}$-$R_{35}$ is 100%.

2. A deuterium-enriched compound of claim 1, wherein the abundance of deuterium in $R_{32}$-$R_{35}$ is 100% and the abundance of deuterium in $R_1$-$R_{35}$ is selected from 20%, 26%, 31%, 37%, 43%, 49%, 54%, 60%, 66%, 71%, 77%, 83%, 89%, 94%, and 100%.

3. A deuterium-enriched compound of claim 1, wherein the abundance of deuterium in $R_{32}$-$R_{35}$ is 100% and the abundance of deuterium in $R_5$-$R_6$ is selected from 50% and 100%.

4. A deuterium-enriched compound of claim 1, wherein the abundance of deuterium in $R_{32}$-$R_{35}$ is 100% and the abundance of deuterium in $R_{22}$-$R_{35}$ is selected from 21%, 29%, 36%, 43%, 50%, 57%, 64%, 71%, 79%, 86%, 93%, and 100%.

5. A deuterium-enriched compound of claim 1, wherein the abundance of deuterium in $R_{32}$-$R_{35}$ is 100% and the abundance of deuterium in $R_7$-$R_{35}$ is selected from 21%, 28%, 34%, 41%, 48%, 55%, 62%, 69%, 76%, 83%, 90%, 97%, and 100%.

6. A deuterium-enriched compound of claim 1, wherein the abundance of deuterium in $R_{32}$-$R_{35}$ is 100% and the abundance of deuterium in $R_5$-$R_6$ and $R_{22}$-$R_{35}$ is selected from 19%, 25%, 31%, 38%, 44%, 50%, 56%, 63%, 69%, 75%, 81%, 88%, 94%, and 100%.

7. A deuterium-enriched compound of claim 1, wherein the abundance of deuterium in $R_{32}$-$R_{35}$ is 100% and the abundance of deuterium in $R_5$-$R_{35}$ is selected from 19%, 26%, 32%, 39%, 45%, 52%, 58%, 65%, 71%, 77%, 84%, 90%, 97%, and 100%.

8. A deuterium-enriched compound of claim 1, wherein the abundance of deuterium in $R_{32}$-$R_{35}$ is 100% and the abundance of deuterium in $R_{13}$-$R_{14}$ is selected from 50% and 100%.

9. A deuterium-enriched compound of claim 1, wherein the abundance of deuterium in $R_{32}$-$R_{35}$ is 100% and the abundance of deuterium in $R_5$-$R_6$ and $R_8$-$R_9$ is selected from 25%, 50%, 75%, and 100%.

10. A deuterium-enriched compound of claim 1, wherein the abundance of deuterium in $R_{32}$-$R_{35}$ is 100% and the abundance of deuterium in $R_{22}$-$R_{26}$ is selected from 20%, 40%, 60%, 80%, and 100%.

11. A deuterium-enriched compound of claim 1, wherein the abundance of deuterium in $R_{32}$-$R_{35}$ is 100% and the abundance of deuterium in $R_{15}$-$R_{21}$ is selected from 14%, 29%, 43%, 57%, 71%, 86%, and 100%.

12. A deuterium-enriched compound of claim 1, wherein the abundance of deuterium in $R_{32}$-$R_{35}$ is 100% and the abundance of deuterium in $R_5$-$R_{14}$ is selected from 10%, 20%, 30%, 40%, and 50%, 60%, 70%, 80%, 90%, and 100%.

13. A deuterium-enriched compound of claim 1, wherein the compound is selected from a compound of Table 1 or a pharmaceutically acceptable salt thereof:

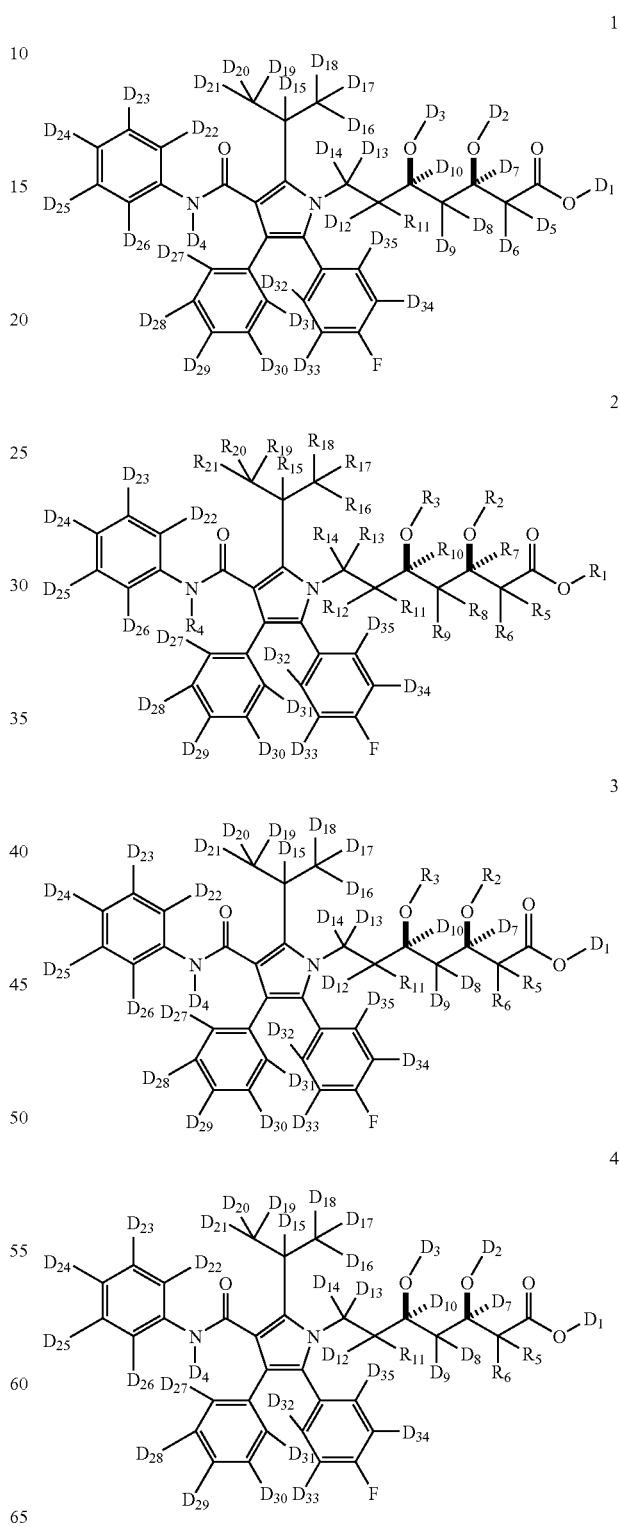

-continued
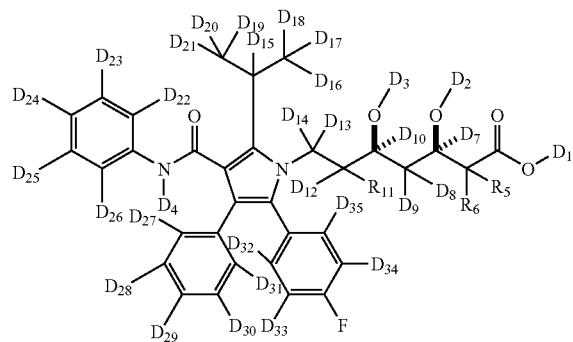
5
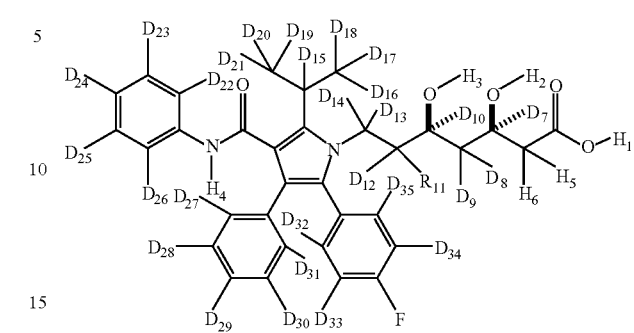
10
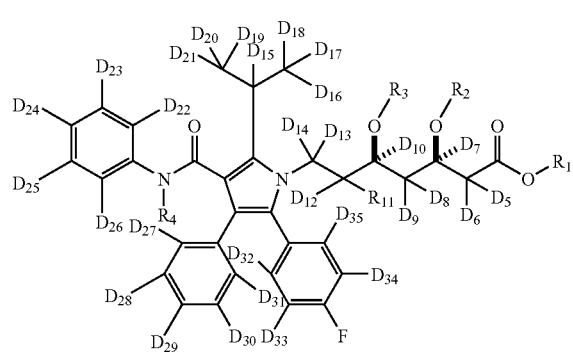
6
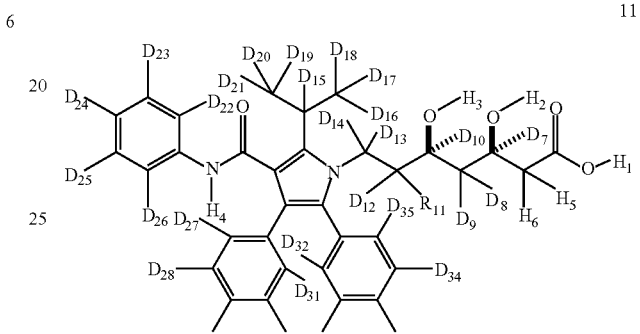
11
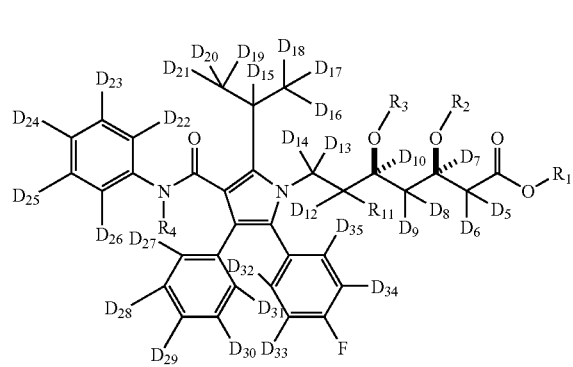
7
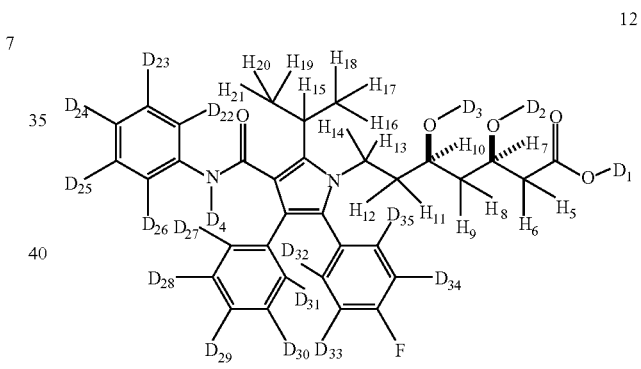
12
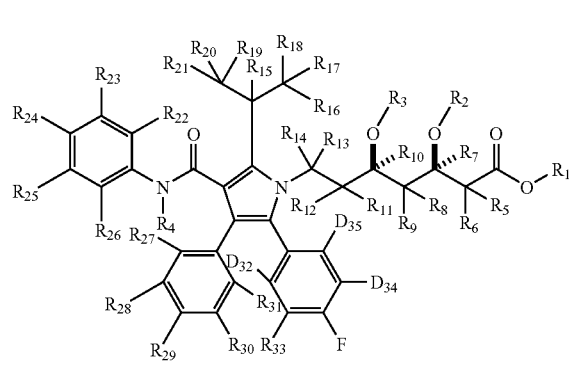
8
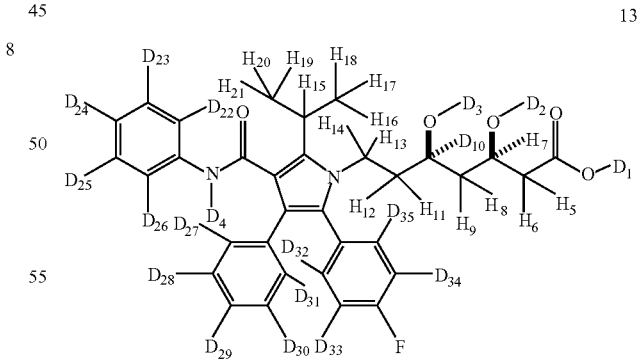
13
wherein when one of $R_1$-$R_{31}$ is present, it is selected from H or D.
14. A deuterium-enriched compound of claim 1, wherein the compound is selected from a compound of Table 2 or a pharmaceutically acceptable salt thereof:

-continued

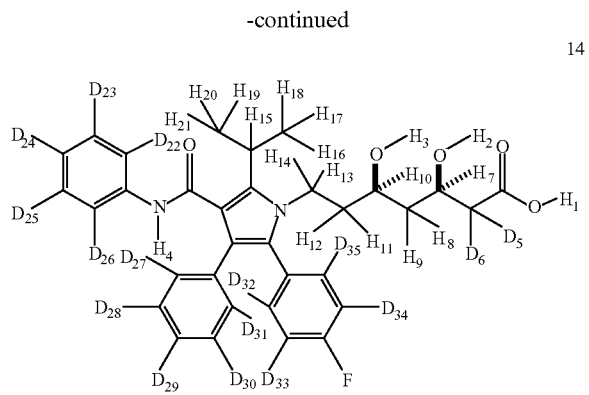
14

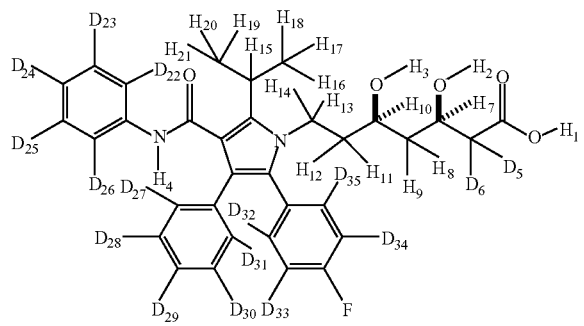
15

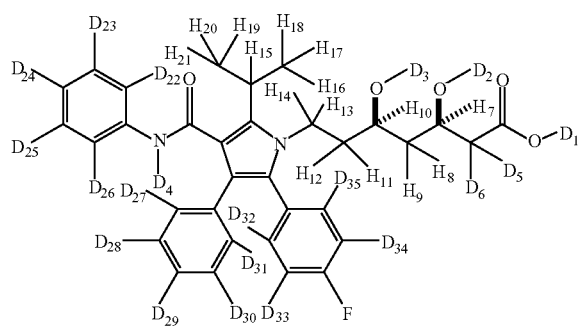
16

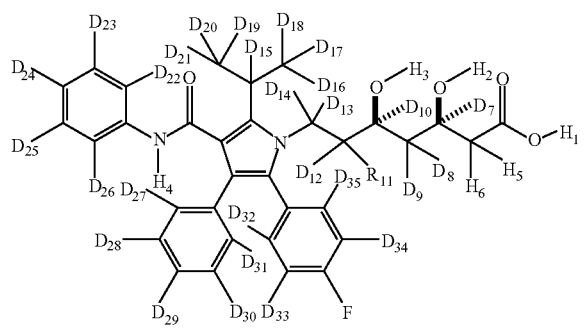
17

-continued

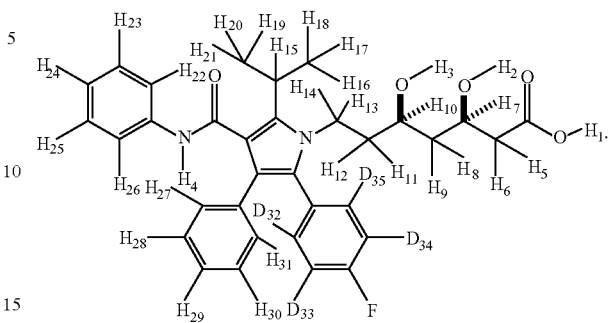
18

15. An isolated deuterium-enriched compound of formula I or a pharmaceutically acceptable salt thereof:

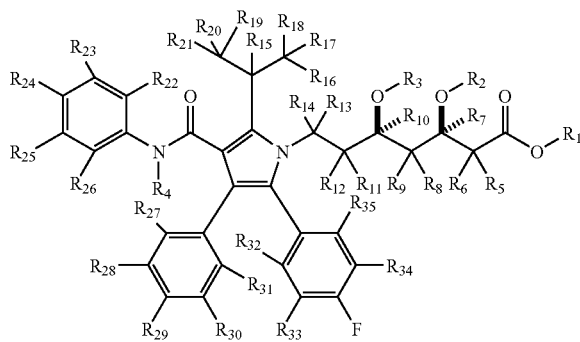
I wherein $R_1$-$R_{35}$ are independently selected from H and D; and the abundance of deuterium in $R_{32}$-$R_{35}$ is 100%.

16. A mixture of deuterium-enriched compounds of formula I or a pharmaceutically acceptable salt thereof:

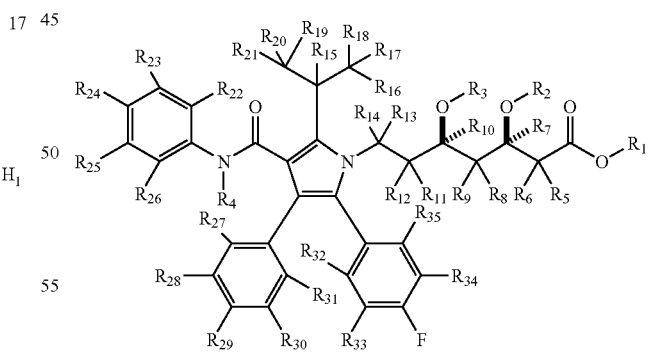
I wherein $R_1$-$R_{35}$ are independently selected from H and D; and the abundance of deuterium in $R_{32}$-$R_{35}$ is 100%.

17. A pharmaceutical composition, comprising: a pharmaceutically acceptable carrier and a therapeutically effective amount of a compound of claim 1 or a pharmaceutically acceptable salt form thereof.

18. A method for treating a disease selected from dyslipidaemia and/or combined hyperlipidemia comprising: administering, to a patient in need thereof, a therapeutically effective amount of a compound of claim 1 or a pharmaceutically acceptable salt form thereof.

19. A deuterium-enriched compound of claim 13, wherein the compound is:

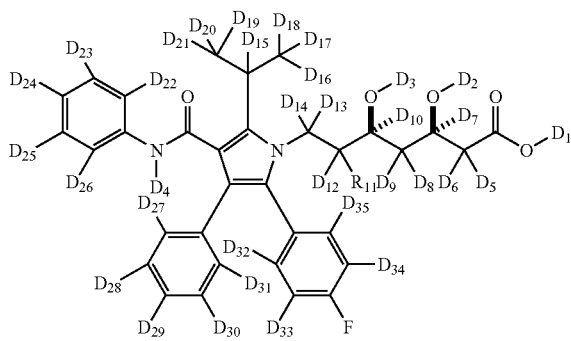

or a pharmaceutically acceptable salt thereof.

20. A deuterium-enriched compound of 13, wherein the compound is:

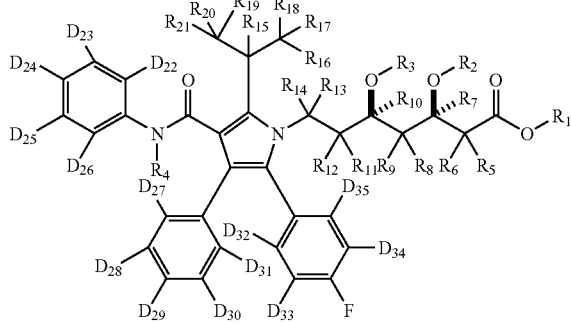

or a pharmaceutically acceptable salt thereof, wherein $R_1$-$R_{21}$ are selected from H and D.

21. A deuterium-enriched compound of 13, wherein the compound is:

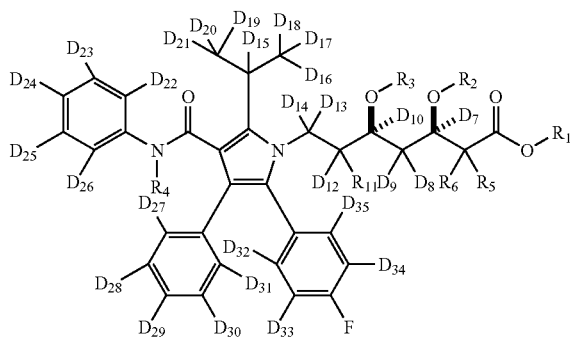

or a pharmaceutically acceptable salt thereof, wherein $R_1$-$R_6$ are selected from H and D.

22. A deuterium-enriched compound of claim 13, wherein the compound is:

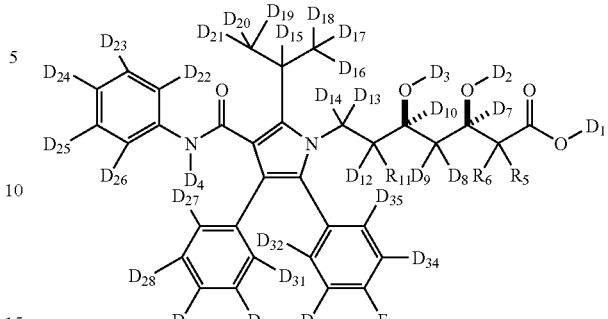

or a pharmaceutically acceptable salt thereof, wherein $R_5$-$R_6$ are selected from H and D.

23. A deuterium-enriched compound of claim 13, wherein the compound is:

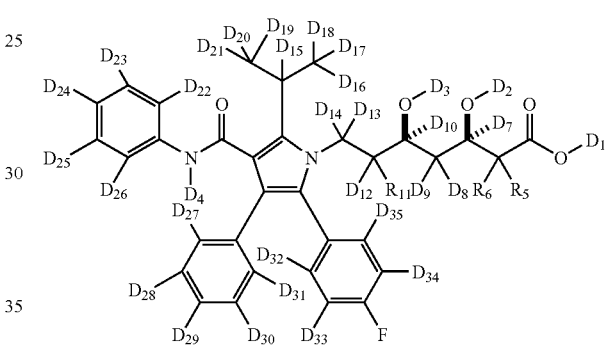

or a pharmaceutically acceptable salt thereof, wherein $R_5$-$R_6$ and $R_{11}$ are selected from H and D.

24. A deuterium-enriched compound of claim 13, wherein the compound is:

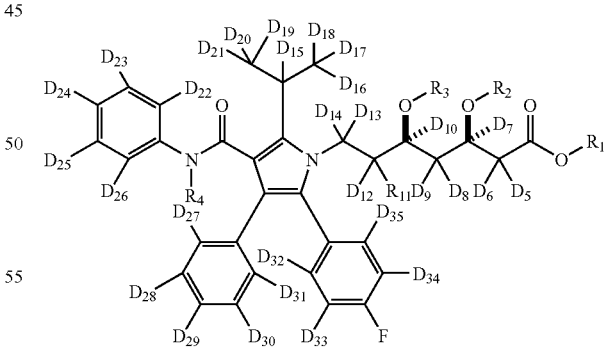

or a pharmaceutically acceptable salt thereof, wherein $R_1$-$R_4$ are selected from H and D.

25. A deuterium-enriched compound of claim 13, wherein the compound is:

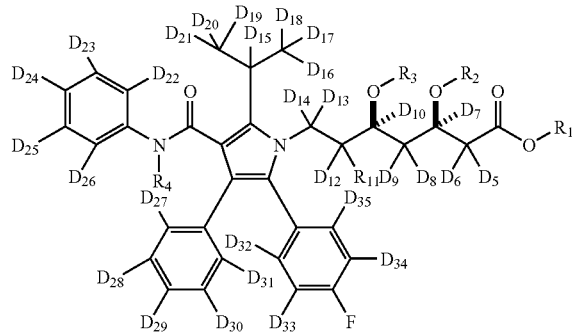

or a pharmaceutically acceptable salt thereof, wherein $R_1$-$R_4$ and $R_{11}$ are selected from H and D.

26. A deuterium-enriched compound of claim 13, wherein the compound is:

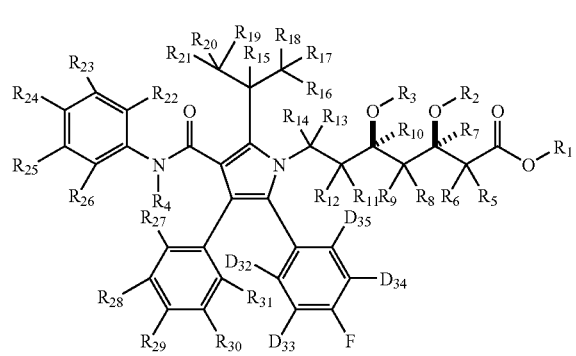

or a pharmaceutically acceptable salt thereof, wherein $R_1$-$R_{31}$ are selected from H and D.

27. A deuterium-enriched compound of claim 14, wherein the compound is:

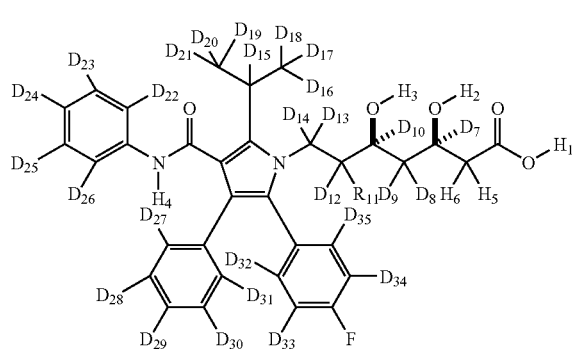

or a pharmaceutically acceptable salt thereof.

28. A deuterium-enriched compound of claim 14, wherein the compound is:

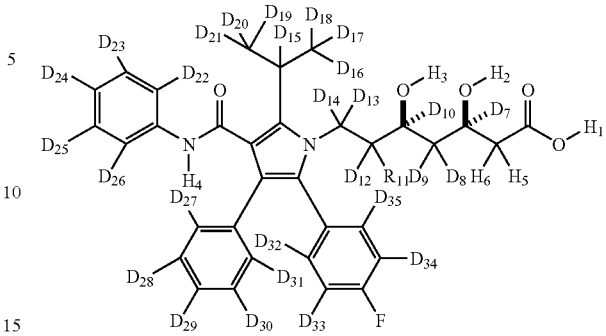

or a pharmaceutically acceptable salt thereof.

29. A deuterium-enriched compound of claim 14, wherein the compound is:

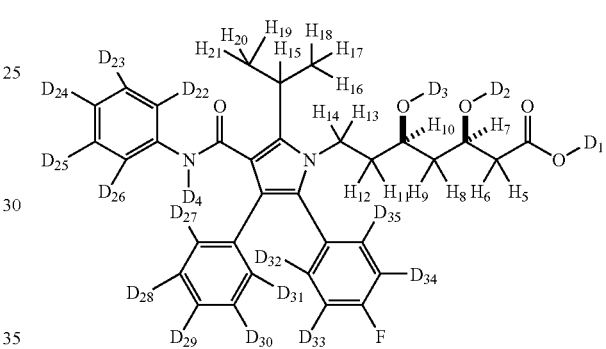

or a pharmaceutically acceptable salt thereof.

30. A deuterium-enriched compound of claim 14, wherein the compound is:

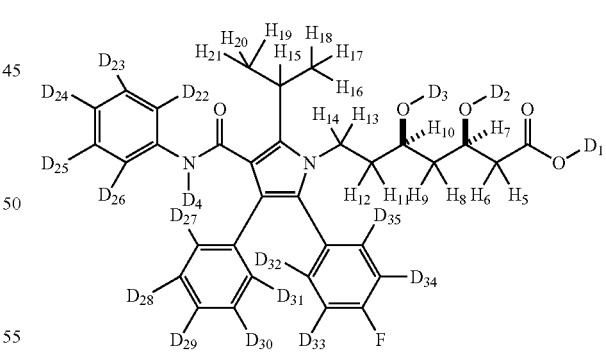

or a pharmaceutically acceptable salt thereof.

31. A deuterium-enriched compound of claim 14, wherein the compound is:

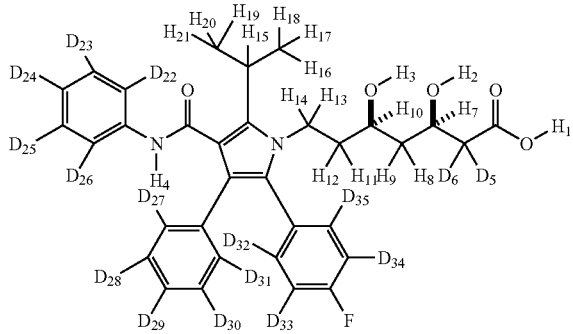

or a pharmaceutically acceptable salt thereof.

32. A deuterium-enriched compound of 14, wherein the compound is:

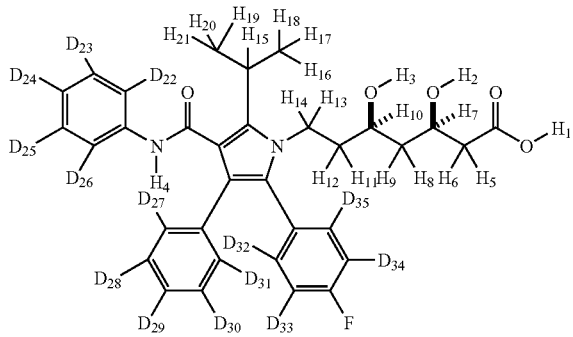

or a pharmaceutically acceptable salt thereof.

33. A deuterium-enriched compound of claim 14, wherein the compound is:

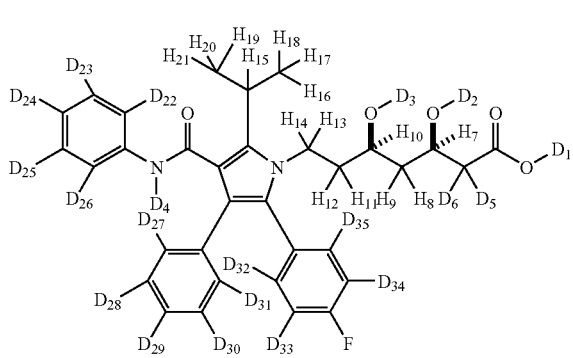

or a pharmaceutically acceptable salt thereof.

34. A deuterium-enriched compound of claim 14, wherein the compound is:

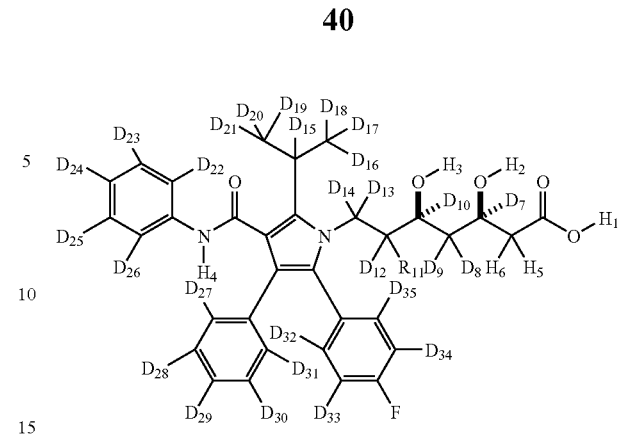

or a pharmaceutically acceptable salt thereof.

35. A deuterium-enriched compound of claim 14, wherein the compound is:

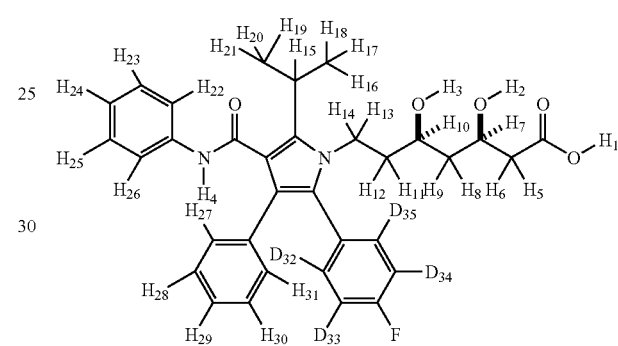

or a pharmaceutically acceptable salt thereof.

36. A pharmaceutical composition, comprising: a pharmaceutically acceptable carrier and a therapeutically effective amount of a compound of claim 2 or a pharmaceutically acceptable salt form thereof.

37. A pharmaceutical composition, comprising: a pharmaceutically acceptable carrier and a therapeutically effective amount of a compound of claim 3 or a pharmaceutically acceptable salt form thereof.

38. A pharmaceutical composition, comprising: a pharmaceutically acceptable carrier and a therapeutically effective amount of a compound of claim 4 or a pharmaceutically acceptable salt form thereof.

39. A pharmaceutical composition, comprising: a pharmaceutically acceptable carrier and a therapeutically effective amount of a compound of claim 5 or a pharmaceutically acceptable salt form thereof.

40. A pharmaceutical composition, comprising: a pharmaceutically acceptable carrier and a therapeutically effective amount of a compound of claim 6 or a pharmaceutically acceptable salt form thereof.

41. A pharmaceutical composition, comprising: a pharmaceutically acceptable carrier and a therapeutically effective amount of a compound of claim 7 or a pharmaceutically acceptable salt form thereof.

42. A pharmaceutical composition, comprising: a pharmaceutically acceptable carrier and a therapeutically effective amount of a compound of claim 8 or a pharmaceutically acceptable salt form thereof.

43. A pharmaceutical composition, comprising: a pharmaceutically acceptable carrier and a therapeutically effective amount of a compound of claim 9 or a pharmaceutically acceptable salt form thereof.

44. A pharmaceutical composition, comprising: a pharmaceutically acceptable carrier and a therapeutically effective amount of a compound of claim 10 or a pharmaceutically acceptable salt form thereof.

45. A pharmaceutical composition, comprising: a pharmaceutically acceptable carrier and a therapeutically effective amount of a compound of claim 11 or a pharmaceutically acceptable salt form thereof.

46. A pharmaceutical composition, comprising: a pharmaceutically acceptable carrier and a therapeutically effective amount of a compound of claim 12 or a pharmaceutically acceptable salt form thereof.

47. A pharmaceutical composition, comprising: a pharmaceutically acceptable carrier and a therapeutically effective amount of a compound of claim 13 or a pharmaceutically acceptable salt form thereof.

48. A pharmaceutical composition, comprising: a pharmaceutically acceptable carrier and a therapeutically effective amount of a compound of claim 14 or a pharmaceutically acceptable salt form thereof.

49. A pharmaceutical composition, comprising: a pharmaceutically acceptable carrier and a therapeutically effective amount of a compound of claim 15 or a pharmaceutically acceptable salt form thereof.

50. A pharmaceutical composition, comprising: a pharmaceutically acceptable carrier and a therapeutically effective amount of a compound of claim 16 or a pharmaceutically acceptable salt form thereof.

51. A pharmaceutical composition, comprising: a pharmaceutically acceptable carrier and a therapeutically effective amount of a compound of claim 19 or a pharmaceutically acceptable salt form thereof.

52. A pharmaceutical composition, comprising: a pharmaceutically acceptable carrier and a therapeutically effective amount of a compound of claim 20 or a pharmaceutically acceptable salt form thereof.

53. A pharmaceutical composition, comprising: a pharmaceutically acceptable carrier and a therapeutically effective amount of a compound of claim 21 or a pharmaceutically acceptable salt form thereof.

54. A pharmaceutical composition, comprising: a pharmaceutically acceptable carrier and a therapeutically effective amount of a compound of claim 22 or a pharmaceutically acceptable salt form thereof.

55. A pharmaceutical composition, comprising: a pharmaceutically acceptable carrier and a therapeutically effective amount of a compound of claim 23 or a pharmaceutically acceptable salt form thereof.

56. A pharmaceutical composition, comprising: a pharmaceutically acceptable carrier and a therapeutically effective amount of a compound of claim 24 or a pharmaceutically acceptable salt form thereof.

57. A pharmaceutical composition, comprising: a pharmaceutically acceptable carrier and a therapeutically effective amount of a compound of claim 25 or a pharmaceutically acceptable salt form thereof.

58. A pharmaceutical composition, comprising: a pharmaceutically acceptable carrier and a therapeutically effective amount of a compound of claim 25 or a pharmaceutically acceptable salt form thereof.

59. A pharmaceutical composition, comprising: a pharmaceutically acceptable carrier and a therapeutically effective amount of a compound of claim 27 or a pharmaceutically acceptable salt form thereof.

60. A pharmaceutical composition, comprising: a pharmaceutically acceptable carrier and a therapeutically effective amount of a compound of claim 28 or a pharmaceutically acceptable salt form thereof.

61. A pharmaceutical composition, comprising: a pharmaceutically acceptable carrier and a therapeutically effective amount of a compound of claim 29 or a pharmaceutically acceptable salt form thereof.

62. A pharmaceutical composition, comprising: a pharmaceutically acceptable carrier and a therapeutically effective amount of a compound of claim 30 or a pharmaceutically acceptable salt form thereof.

63. A pharmaceutical composition, comprising: a pharmaceutically acceptable carrier and a therapeutically effective amount of a compound of claim 31 or a pharmaceutically acceptable salt form thereof.

64. A pharmaceutical composition, comprising: a pharmaceutically acceptable carrier and a therapeutically effective amount of a compound of claim 32 or a pharmaceutically acceptable salt form thereof.

65. A pharmaceutical composition, comprising: a pharmaceutically acceptable carrier and a therapeutically effective amount of a compound of claim 33 or a pharmaceutically acceptable salt form thereof.

66. A pharmaceutical composition, comprising: a pharmaceutically acceptable carrier and a therapeutically effective amount of a compound of claim 34 or a pharmaceutically acceptable salt form thereof.

67. A pharmaceutical composition, comprising: a pharmaceutically acceptable carrier and a therapeutically effective amount of a compound of claim 35 or a pharmaceutically acceptable salt form thereof.

68. A method for treating a disease selected from dyslipidaemia and/or combined hyperlipidemia comprising: administering, to a patient in need thereof, a therapeutically effective amount of a compound of claim 2 or a pharmaceutically acceptable salt form thereof.

69. A method for treating a disease selected from dyslipidaemia and/or combined hyperlipidemia comprising: administering, to a patient in need thereof, a therapeutically effective amount of a compound of claim 3 or a pharmaceutically acceptable salt form thereof.

70. A method for treating a disease selected from dyslipidaemia and/or combined hyperlipidemia comprising: administering, to a patient in need thereof, a therapeutically effective amount of a compound of claim 4 or a pharmaceutically acceptable salt form thereof.

71. A method for treating a disease selected from dyslipidaemia and/or combined hyperlipidemia comprising: administering, to a patient in need thereof, a therapeutically effective amount of a compound of claim 5 or a pharmaceutically acceptable salt form thereof.

72. A method for treating a disease selected from dyslipidaemia and/or combined hyperlipidemia comprising: administering, to a patient in need thereof, a therapeutically effective amount of a compound of claim 6 or a pharmaceutically acceptable salt form thereof.

73. A method for treating a disease selected from dyslipidaemia and/or combined hyperlipidemia comprising: administering, to a patient in need thereof, a therapeutically effective amount of a compound of claim 7 or a pharmaceutically acceptable salt form thereof.

74. A method for treating a disease selected from dyslipidaemia and/or combined hyperlipidemia comprising: administering, to a patient in need thereof, a therapeutically effective amount of a compound of claim 8 or a pharmaceutically acceptable salt form thereof.

75. A method for treating a disease selected from dyslipidaemia and/or combined hyperlipidemia comprising: administering, to a patient in need thereof, a therapeutically effective amount of a compound of claim 9 or a pharmaceutically acceptable salt form thereof.

76. A method for treating a disease selected from dyslipidaemia and/or combined hyperlipidemia comprising: administering, to a patient in need thereof, a therapeutically effective amount of a compound of claim 10 or a pharmaceutically acceptable salt form thereof.

77. A method for treating a disease selected from dyslipidaemia and/or combined hyperlipidemia comprising: administering, to a patient in need thereof, a therapeutically effective amount of a compound of claim 11 or a pharmaceutically acceptable salt form thereof.

78. A method for treating a disease selected from dyslipidaemia and/or combined hyperlipidemia comprising: administering, to a patient in need thereof, a therapeutically effective amount of a compound of claim 12 or a pharmaceutically acceptable salt form thereof.

79. A method for treating a disease selected from dyslipidaemia and/or combined hyperlipidemia comprising: administering, to a patient in need thereof, a therapeutically effective amount of a compound of claim 13 or a pharmaceutically acceptable salt form thereof.

80. A method for treating a disease selected from dyslipidaemia and/or combined hyperlipidemia comprising: administering, to a patient in need thereof, a therapeutically effective amount of a compound of claim 14 or a pharmaceutically acceptable salt form thereof.

81. A method for treating a disease selected from dyslipidaemia and/or combined hyperlipidemia comprising: administering, to a patient in need thereof, a therapeutically effective amount of a compound of claim 15 or a pharmaceutically acceptable salt form thereof.

82. A method for treating a disease selected from dyslipidaemia and/or combined hyperlipidemia comprising: administering, to a patient in need thereof, a therapeutically effective amount of a compound of claim 16 or a pharmaceutically acceptable salt form thereof.

83. A method for treating a disease selected from dyslipidaemia and/or combined hyperlipidemia comprising: administering, to a patient in need thereof, a therapeutically effective amount of a compound of claim 19 or a pharmaceutically acceptable salt form thereof.

84. A method for treating a disease selected from dyslipidaemia and/or combined hyperlipidemia comprising: administering, to a patient in need thereof, a therapeutically effective amount of a compound of claim 20 or a pharmaceutically acceptable salt form thereof.

85. A method for treating a disease selected from dyslipidaemia and/or combined hyperlipidemia comprising: administering, to a patient in need thereof, a therapeutically effective amount of a compound of claim 21 or a pharmaceutically acceptable salt form thereof.

86. A method for treating a disease selected from dyslipidaemia and/or combined hyperlipidemia comprising: administering, to a patient in need thereof, a therapeutically effective amount of a compound of claim 22 or a pharmaceutically acceptable salt form thereof.

87. A method for treating a disease selected from dyslipidaemia and/or combined hyperlipidemia comprising: administering, to a patient in need thereof, a therapeutically effective amount of a compound of claim 23 or a pharmaceutically acceptable salt form thereof.

88. A method for treating a disease selected from dyslipidaemia and/or combined hyperlipidemia comprising: administering, to a patient in need thereof, a therapeutically effective amount of a compound of claim 24 or a pharmaceutically acceptable salt form thereof.

89. A method for treating a disease selected from dyslipidaemia and/or combined hyperlipidemia comprising: administering, to a patient in need thereof, a therapeutically effective amount of a compound of claim 25 or a pharmaceutically acceptable salt form thereof.

90. A method for treating a disease selected from dyslipidaemia and/or combined hyperlipidemia comprising: administering, to a patient in need thereof, a therapeutically effective amount of a compound of claim 25 or a pharmaceutically acceptable salt form thereof.

91. A method for treating a disease selected from dyslipidaemia and/or combined hyperlipidemia comprising: administering, to a patient in need thereof, a therapeutically effective amount of a compound of claim 27 or a pharmaceutically acceptable salt form thereof.

92. A method for treating a disease selected from dyslipidaemia and/or combined hyperlipidemia comprising: administering, to a patient in need thereof, a therapeutically effective amount of a compound of claim 28 or a pharmaceutically acceptable salt form thereof.

93. A method for treating a disease selected from dyslipidaemia and/or combined hyperlipidemia comprising: administering, to a patient in need thereof, a therapeutically effective amount of a compound of claim 29 or a pharmaceutically acceptable salt form thereof.

94. A method for treating a disease selected from dyslipidaemia and/or combined hyperlipidemia comprising: administering, to a patient in need thereof, a therapeutically effective amount of a compound of claim 30 or a pharmaceutically acceptable salt form thereof.

95. A method for treating a disease selected from dyslipidaemia and/or combined hyperlipidemia comprising: administering, to a patient in need thereof, a therapeutically effective amount of a compound of claim 31 or a pharmaceutically acceptable salt form thereof.

96. A method for treating a disease selected from dyslipidaemia and/or combined hyperlipidemia comprising: administering, to a patient in need thereof, a therapeutically effective amount of a compound of claim 32 or a pharmaceutically acceptable salt form thereof.

97. A method for treating a disease selected from dyslipidaemia and/or combined hyperlipidemia comprising: administering, to a patient in need thereof, a therapeutically effective amount of a compound of claim 33 or a pharmaceutically acceptable salt form thereof.

98. A method for treating a disease selected from dyslipidaemia and/or combined hyperlipidemia comprising: administering, to a patient in need thereof, a therapeutically effective amount of a compound of claim 34 or a pharmaceutically acceptable salt form thereof.

99. A method for treating a disease selected from dyslipidaemia and/or combined hyperlipidemia comprising: administering, to a patient in need thereof, a therapeutically effective amount of a compound of claim 35 or a pharmaceutically acceptable salt form thereof.

* * * * *